United States Patent
Pfeiler et al.

(10) Patent No.: US 12,076,584 B2
(45) Date of Patent: Sep. 3, 2024

(54) ANALYSIS OF DOSE RATE ROBUSTNESS AGAINST UNCERTAINTIES IN RADIATION TREATMENT PLANNING

(71) Applicants: Varian Medical Systems Particle Therapy GmbH & Co, KG, Troisdorf (DE); Varian Medical Systems International AG, Cham (CH)

(72) Inventors: Tina Pfeiler, Cologne (DE); Reynald Vanderstraeten, Uccle (BE); Michiko Rossi, Espoo (FI); Isabel Huth, Kuerten (DE); Viljo Petaja, Espoo (FI)

(73) Assignees: VARIAN MEDICAL SYSTEMS PARTICLE THERAPY GMBH & CO, KG, Troisdorf (DE); SIEMENS HEALTHINEERS INTERNATIONAL AG, Steinhausen (CH)

( * ) Notice: Subject to any disclaimer, the term of this patent is extended or adjusted under 35 U.S.C. 154(b) by 219 days.

(21) Appl. No.: 17/364,663

(22) Filed: Jun. 30, 2021

(65) Prior Publication Data

US 2023/0001233 A1   Jan. 5, 2023

(51) Int. Cl.
*A61N 5/10* (2006.01)
*G21K 5/04* (2006.01)

(52) U.S. Cl.
CPC ......... *A61N 5/1031* (2013.01); *A61N 5/1071* (2013.01); *G21K 5/04* (2013.01);
(Continued)

(58) Field of Classification Search
CPC ........ A61N 5/10; A61N 5/103; A61N 5/1031; A61N 5/1071; A61N 2005/1034; A61N 2005/1087; A61N 2005/1089; G21K 5/04
See application file for complete search history.

(56) References Cited

U.S. PATENT DOCUMENTS

| | | | |
|---|---|---|---|
| 2004/0071261 A1* | 4/2004 | Earl | A61N 5/1047 378/65 |
| 2017/0014642 A1* | 1/2017 | An | A61N 5/1031 |

(Continued)

FOREIGN PATENT DOCUMENTS

| | | | | |
|---|---|---|---|---|
| JP | 2018187089 | | 11/2018 | |
| WO | WO-2015051807 A1 * | | 4/2015 | ........... A61N 5/1001 |
| WO | 2022077160 | | 4/2022 | |

OTHER PUBLICATIONS

Reindl, J., & Girst, S. (2019). PMB flash—status and perspectives of combining proton minibeam with flash radiotherapy. Journal of Cancer Immunology, (1), 14-23. https://doi.org/10.33696/cancerimmunol.1.003 (Year: 2019).*

Gao, H., Lin, B., Lin, Y., Fu, S., Langen, K., Liu, T., & Bradley, J. (2020). Simultaneous dose and dose rate optimization (SDDRO) for Flash Proton therapy. Medical Physics, 47(12), 6388-6395. https://doi.org/10.1002/mp.14531 (Year: 2020).*

(Continued)

*Primary Examiner* — Christine H Matthews
*Assistant Examiner* — Marc D. Honrath
(74) *Attorney, Agent, or Firm* — Harness, Dickey & Pierce, P.L.C.

(57) ABSTRACT

Presented systems and methods enable efficient and effective robust radiation treatment planning and treatment, including analysis of dose rate robustness. In one embodiment, a method comprising accessing treatment plan information, accessing information corresponding to an uncertainty associated with implementation of the radiation treatment plan, and generating a histogram, wherein the histogram conveys a characteristic of the treatment plan including an impact of the uncertainty on the characteristic. The histogram can be a dose rate volume histogram and can be utilized to test a degree of robustness of a treatment plan (e.g., including allowance for uncertainty scenarios, etc.). The uncertainty can be associated with potential variation associated with tolerances (e.g., radiation system/machine performance tolerance, patient characteristic tolerances, etc.) and set up (Continued)

issues (e.g., variation in initial system/machine set up, variation patient setup/position, etc.).

21 Claims, 20 Drawing Sheets

(52) U.S. Cl.
CPC ............... *A61N 2005/1034* (2013.01); *A61N 2005/1087* (2013.01); *A61N 2005/1089* (2013.01)

(56) References Cited

U.S. PATENT DOCUMENTS

| | | | |
|---|---|---|---|
| 2018/0099151 A1* | 4/2018 | Sullivan | A61N 5/1039 |
| 2021/0228907 A1* | 7/2021 | Olcott | A61N 5/1045 |

OTHER PUBLICATIONS

Van Marlen, P., Dahele, M., Folkerts, & M., Abel. (2020). Bringing flash to the clinic: Treatment planning considerations for ultrahigh dose-rate proton beams. International Journal of Radiation Oncology*Biology*Physics, 106(3), 621-629. 10.1016/j.ijrobp.2019.11.011 (Year: 2020).*

Alexei Trofimov et al., "Visualization of a variety of possible dosimetric outcomes in radiation therapy using dose-volume histogram bands", Practical Radiation Oncology, vol. 2, No. 3, Jul. 1, 2012, pp. 164-171.

Favaudon, V. et al. (2014). Ultrahigh dose-rate Flash irradiation increases the differential response between normal and tumor tissue in mice. Science Translational Medicine, 6(245).

Vozenin, M. et al. (2019). Biological benefits of ultra-high dose rate Flash radiotherapy: Sleeping Beauty awoken. Clinical Oncology, 31(7), 407-415.

* cited by examiner

```
1200
```

- 1202 ACCESS INFORMATION IN COMPUTER SYSTEM MEMORY
- 1204 ASSOCIATE A VALUE OF AN ATTRIBUTE WITH EACH SUB-VOLUME OF A TARGET VOLUME
- 1206 RENDER AND DISPLAY EACH SUB-VOLUME ACCORDING TO THE VALUE

- 1302 ACCESS INFORMATION IN COMPUTER SYSTEM MEMORY
- 1304 GENERATE A HISTOGRAM FOR A TARGET VOLUME
- 1306 DISPLAY THE HISTOGRAM

Fig. 13

| | ID/Type | cm³ | Vol[%] | Dose [Gy] | Actual Dose [Gy] | Priority | RO | gEUD a | |
|---|---|---|---|---|---|---|---|---|---|
| | Upper | 0.0 | 0.0 | 56.81 | 67.00 | 100 | √ | | X |
| | Upper | 0.0 | 0.0 | 60.05 | 67.00 | 130 | √ | | X |
| | Lower | 110.9 | 99.5 | 54.32 | 53.84 | 200 | √ | | X |
| | CTVO | 103.6 | | | | | | | |
| | Upper | 0.0 | 0.0 | 65.93 | 75.36 | 130 | √ | | X |
| | Upper | 0.0 | 0.0 | 64.15 | 75.36 | 100 | √ | | X |
| | Lower | 110.9 | 99.5 | 59.64 | 58.72 | 200 | √ | | X |
| | BrainSca | 25.6 | | | | | | | |
| | Upper | 0.0 | 0.0 | 37.00 | 38.53 | 120 | √ | | X |
| | Line | 25.5 | | | | 35 | ● | | X |
| | CPAP | 103.5 | | | | | | | |
| | Upper | 0.0 | 0.0 | | | | | | X |
| | Line | 0.0 | | | | 90 | ● | | X |

1910
Accessing information regarding a treatment plan.

1920
Accessing information corresponding to uncertainties associated with the treatment plan.

1930
Performing an optimization process based on the treatment plan information and uncertainty information and generating graphical element information that conveys the results of the optimization process and potential impact of the uncertainties.

1940
Finalizing the treatment plan.

FIG 19

ANALYSIS OF DOSE RATE ROBUSTNESS AGAINST UNCERTAINTIES IN RADIATION TREATMENT PLANNING

BACKGROUND

Radiation therapy is utilized in various medical treatments. Typically, radiation therapy involves directing a beam of high energy proton, photon, ion, or electron radiation ("therapeutic radiation") into a target or target volume (e.g., a tissue volume that includes a tumor, lesion, etc.).

Typically, before a patient is treated with radiation, a treatment plan specific to that patient is developed. The plan usually defines various aspects of the therapy using simulations and optimizations based on past experiences. In general, the purpose of the treatment plan is to deliver sufficient radiation to the unhealthy tissue while minimizing exposure of surrounding healthy tissue to the radiation.

Usually, the planner's goal is to find a solution that is optimal with respect to multiple clinical goals. The clinical goals may be contradictory in the sense that an improvement toward one goal may have a detrimental effect on reaching another goal. For example, a treatment plan that spares the liver from receiving a dose of radiation may result in the stomach receiving too much radiation. These types of tradeoffs often lead to an iterative process in which the planner creates different plans to find the plan that is best suited to achieving the desired outcome.

Recent radiobiology approaches have demonstrated a desirable effectiveness of delivering an entire, relatively high therapeutic radiation dose to a target within a single short period of time. For example, a target can be treated with multiple radiation beams, with each beam delivering at least 40 Grays in less than or equal to one second (e.g., 40 Gy/s, etc.), and may deliver much more (e.g., 50 Gy, 100 Gy, etc.) in less than one second. This type of treatment is referred to generally herein as FLASH radiation therapy (FLASH RT).

Evidence to date suggests that FLASH RT is effective at treating target tissue, while advantageously sparing normal healthy tissue from damage. The effectiveness of FLASH is highly tied to the new dose rate scheme of exposing tissue to a high radiation dose for only a very short period of time, and thus introduces important dose and dose rate constraints and issues that are not typically considered in or achieved with conventional radiation treatment planning.

SUMMARY

Presented systems and methods enable efficient and effective radiation treatment planning and treatment for high radiation rate approaches, including considering and adjusting for various uncertainties. In one embodiment, a computer system, comprises a processor and a memory configured to perform radiation treatment methods (e.g., a treatment plan uncertainty adjustment method, etc.). The memory is coupled to the processor and includes instructions that, when executed, cause the processor to perform the method. In one embodiment the method comprises accessing information associated with a treatment plan, accessing information corresponding to an uncertainty associated with implementation of the radiation treatment plan, and performing an optimization process including generating a graphical element, wherein the graphical element conveys results of the optimization process including an impact of the uncertainty. The graphical element can be a histogram. The histogram can be a dose rate volume histogram with a volume indication on a first axis and a dose rate indication on a second axis.

It is appreciated there can be different types of uncertainties. The uncertainty can be associated with a radiation system performance tolerance. The uncertainty can be associated with a patient set up. The uncertainty can include a tolerance variance associated with a parameter that impacts a dose rate. The method can also include finalizing the radiation treatment plan, including evaluating information associated with the graphical element and analyzing robustness of the treatment plan against uncertainties.

In one embodiment, a non-transitory computer-readable storage medium has computer-executable instructions for causing a computer system to perform a method comprising: ascertaining treatment plan information and corresponding uncertainty information associated with a target volume, generating a histogram of a plurality of uncertainty adjusted optimized dose rates for the target volume and organs at risk in accordance with the treatment plan information and corresponding uncertainty information, and evaluating the histogram results. The histogram can be utilized to test a degree of robustness of a treatment plan (e.g., including allowance for uncertainty scenarios, etc.). Generating a histogram can include generating a plurality of graphs, wherein respective ones of the plurality of graphs correspond to respective ones of a plurality of uncertainties. The plurality of uncertainties can be the basis for the plurality of uncertainty adjusted optimized dose rates.

The plurality of graphs can correspond to a dose rate band which defines a region in which a graph curve for an actual treatment lies. In one exemplary implementation, a proportion of irradiated volume receiving a threshold dose rate Dth and the dose rate received by (100–p) percent of the volume is displayed for uncertainty scenarios associated with the histogram. The uncertainty information can be associated with at least one of radiation system performance tolerances, position of a treatment target, a beam intensity scenario, a range uncertainty, different transmission tables, and spot times (e.g., pencil beam scanning in particle therapy). The histogram can be included in graphical user interface (GUI). Evaluating the histogram results can include analyzing if a dose rate prescription is met for the target and healthy tissue.

In one embodiment, a radiation system comprises an accelerator and a control component. The accelerator is configured to generate radiation and direct the radiation towards a treatment target. The control component is configured to control the accelerator in accordance with a treatment plan, wherein the treatment plan is generated in accordance with a radiation treatment planning method including uncertainty scenario analysis. In one exemplary implementation, the radiation treatment planning method comprises ascertaining treatment plan and uncertainty scenario information, determining a dose rate distribution based upon the uncertainty scenario information, and generating a histogram visualization of the dose rate distribution based upon the uncertainty scenario information. The radiation treatment planning method can include displaying a dose rate volume histogram and parameters are shown for regions of interest.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

FIGS. 12 and 13 are flowcharts of examples of computer-implemented operations for generating GUIs in an embodiment according to the present invention.

FIG. 16 is a graphical representation of a multifield optimization dose volume histogram in accordance with one embodiment.

FIG. 19 is a flow chart of treatment plan uncertainty adjustment method in accordance with one embodiment.

DETAILED DESCRIPTION

Figure 1:
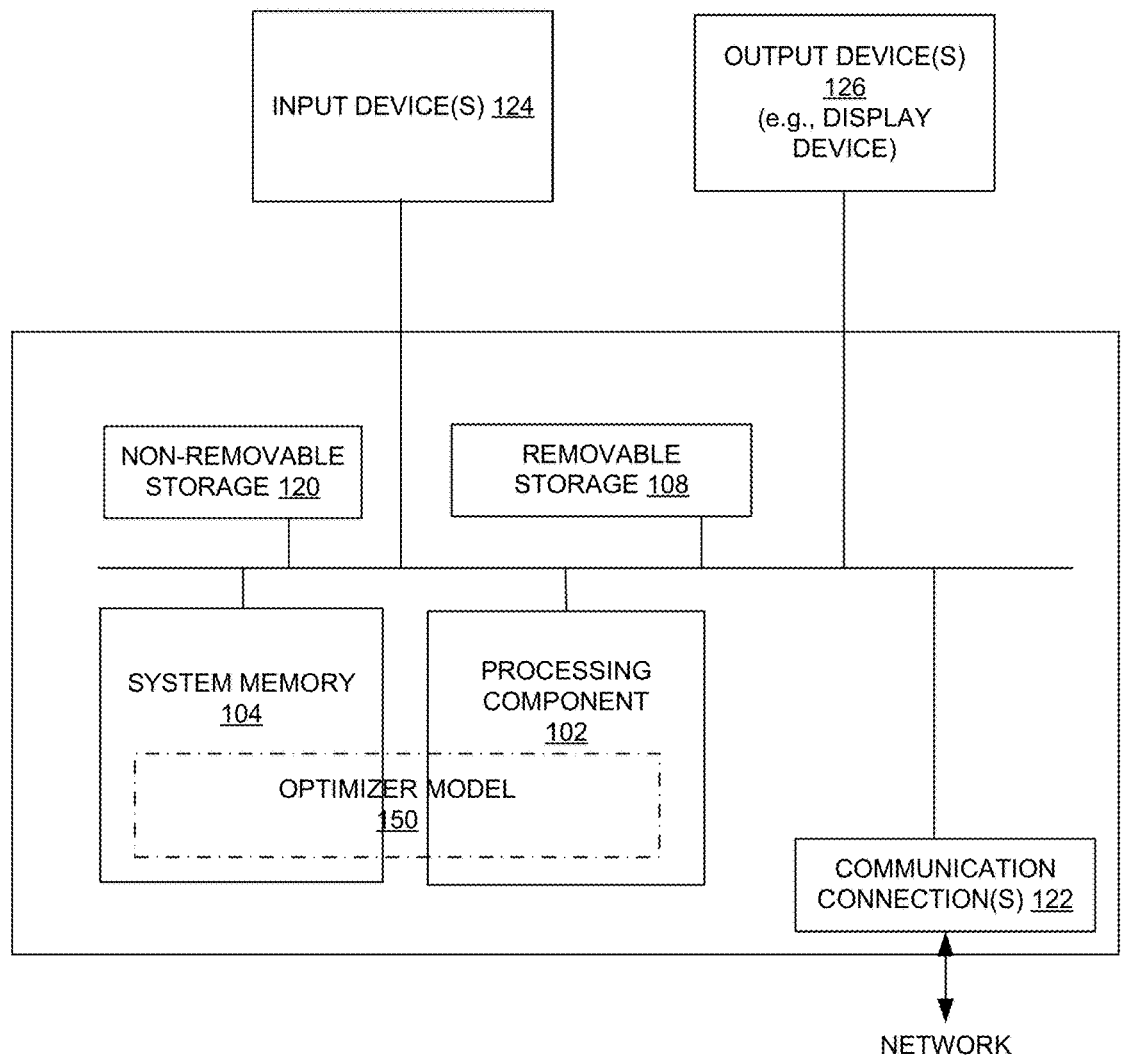
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "generating," "representing," "applying," "indicating," "storing," "using," "adjusting," "including," "computing," "displaying," "associating," "rendering," "determining," or the like, refer to actions and processes (e.g., the flowcharts of FIGS. 8, 10, 12, and 13) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices. Terms such as "dose" or "dose rate" or "fluence" generally refer to a dose value or dose rate value or fluence value, respectively; the use of such terms will be clear from the context of the surrounding discussion.

Portions of the detailed description that follows are presented and discussed in terms of methods. Although steps and sequencing thereof are disclosed in figures herein (e.g., FIGS. 8, 10, 12, and 13) describing the operations of those methods, such steps and sequencing are examples only. Embodiments are well suited to performing various other steps or variations of the steps recited in the flowcharts of the figures herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Radiation Treatment Planning Using Different Types of Histograms

Various types of radiation treatment processes usually include radiation treatment planning. In some radiation therapy techniques the intensity of the particle beam is either constant or modulated across a field of delivery (e.g., intensity modulated radiation therapy (IMRT), intensity modulated particle therapy (IMPT), etc.) and beam intensity is varied across treatment regions (e.g., target volumes, etc.) in a patient. Depending on the treatment modality, the degrees of freedom available for intensity modulation can include beam shaping (e.g., via collimation, etc.), beam weighting (e.g., via spot scanning, etc.), and angle of incidence (which may be referred to as beam geometry). These degrees of freedom can lead to an effectively infinite number of potential treatment plans, and therefore consistently and efficiently generating and evaluating high-quality treatment plans is beyond the capability of a human. Effective development of practical treatment plans relies on the use of a various systems (e.g., computer systems, radiation systems, specialized systems, etc.), particularly considering the time constraints associated with the use of radiation therapy to treat ailments like cancer, as well as the large number of patients that are undergoing or need to undergo radiation therapy during any given time period.

Presented systems and methods can enable efficient and effective radiation treatment planning and treatment for high radiation rate approaches (e.g., FLASH RT, etc.). In one embodiment, a dose rate-volume histogram (different from a dose-volume histogram) is generated for a target volume. The dose rate-volume histogram indicates dose rates and percentages of the target volume that receive the dose rates. The dose rate-volume histogram can be stored in computer system memory and used to generate a radiation treatment plan. Values of parameters that can have an effect on a dose rate can be adjusted until the dose rate-volume histogram satisfies objectives associated with the radiation treatment plan.

It is appreciated there can be various different parameters that can have an effect on a dose rate. In one embodiment, the parameters can include a number of irradiations of the target volume, a duration of each of the irradiations, and a dose deposited in each of the irradiations. The parameters can include directions of beams to be directed into the target volume, and beam energies for each of the beams. The parameters can also include a period of time during which the irradiations are applied (e.g., the irradiations are intermittently applied over a period of time, such as an hour, etc.), and an interval of time between each of the periods of irradiations (e.g., each hour-long period is separated by a day, etc.).

In one embodiment, an irradiation time-volume histogram (also different from a dose-volume histogram) is generated for the target volume. The irradiation time-volume histogram indicates irradiation times (durations) and percentages of the target volume that are irradiated for those amounts of time. The irradiation time-volume histogram can be stored in computer system memory and used in the generation of a radiation treatment plan. Values of parameters that can have an effect on irradiation time can be adjusted until the irradiation time-volume histogram satisfies objectives associated with the radiation treatment plan.

Various combinations of histograms, (e.g., a dose rate-volume histogram, an irradiation time-volume histogram, both, etc.) can be generated, evaluated, and used to generate a radiation treatment plan.

It is appreciated that different uncertainty scenarios (e.g., associated with tolerances in patient positioning, machine performance, etc.) can arise during treatment. In one embodiment, consideration of different uncertainty scenarios and adjustments based on the results can be implemented. In one exemplary implementation, dose volume histograms (DVHs) and dose rate volume histograms (DRVHs) relating doses and dose rates, respectively, to tissue volumes are calculated, displayed and visualized for different uncertainty scenarios. Additional description of different uncertainty scenarios and impacts on various aspects (e.g., doses, DVHs, DRVHs, etc.) of radiation planning and treatment are set forth below in later paragraphs of this detailed description.

In one embodiment, a graphical user interface (GUI) that includes a representation of a target volume and sub-volumes of the target volume is rendered and displayed. Information that includes a dose rate received by each sub-volume is accessed (e.g., information stored in a computer system memory, etc.). In one exemplary implementation, a value of an attribute is associated with each sub-volume, where the value corresponds to an amount of the dose rate received by that sub-volume. Each sub-volume can then be rendered according to that value. The rendering of the target volume can be a two-dimensional cross-section of the target volume or a virtual three-dimensional representation of the target volume.

In one embodiment, the GUI can include a dose rate-volume histogram. The GUI can include an irradiation time-volume histogram for the target volume.

Presented systems and methods can improve radiation treatment planning and the treatment itself by expanding treatment (e.g., FLASH RT, etc.) to a wider variety of treatment platforms and target sites (e.g., tumors, etc.). Treatment plans generated as described herein are superior for sparing healthy tissue from radiation in comparison to conventional techniques for FLASH dose rates by optimizing the balance between the dose rate delivered to unhealthy tissue (e.g., a tumor, etc.) in a target volume and the dose rate delivered to surrounding healthy tissue. When used with FLASH dose rates, management of patient motion can be simplified because the doses are applied in a short period of time (e.g., less than a second). Treatment planning, while still a complex task, is improved relative to conventional treatment planning. In addition to these benefits, presented GUI capabilities facilitate treatment planning by allowing a planner to readily visualize key elements of a proposed treatment plan (e.g., the dose rate per sub-volume, etc.), to readily visualize the effects on those elements of changes to the proposed plan, to readily visualize impacts of treatment uncertainty scenarios, and to readily visualize a comparison between different plans.

FIG. 1 is a block diagram of an exemplary computer system 100 in accordance with one embodiment. In a basic configuration, the system 100 includes a processing component 102 and memory 104. The system 100 can also have additional features and functionality. For example, the system 100 can include additional various types of storage (e.g., removable, non-removable, magnetic, optical disks, tape, etc.). Such additional storage is illustrated in FIG. 1 by removable storage 108 and non-removable storage 120. The system 100 can contain communications connection(s) 122 that allow the device to communicate with other devices (e.g., in a networked environment using logical connections to remote computers, etc.). In one exemplary implementation, the system 100 includes input device(s) 124 (e.g., keyboard, mouse, pen, voice input device, touch input device, etc.) configured to input information and output device(s) 126 (e.g., a display device, speakers, printer, etc.) configured to input information. A display device may be, for example, a cathode ray tube display, a light-emitting diode display, or a liquid crystal display. Information can be input/output from various sources (e.g., a user, physician, clinician, technician, other system, etc.)

In the example of FIG. 1, information associate with optimizer model 150 is stored in memory 104 and implemented by processing component 102. The memory 104 includes computer-readable instructions, data structures, program modules, and the like, associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

Figure 2:
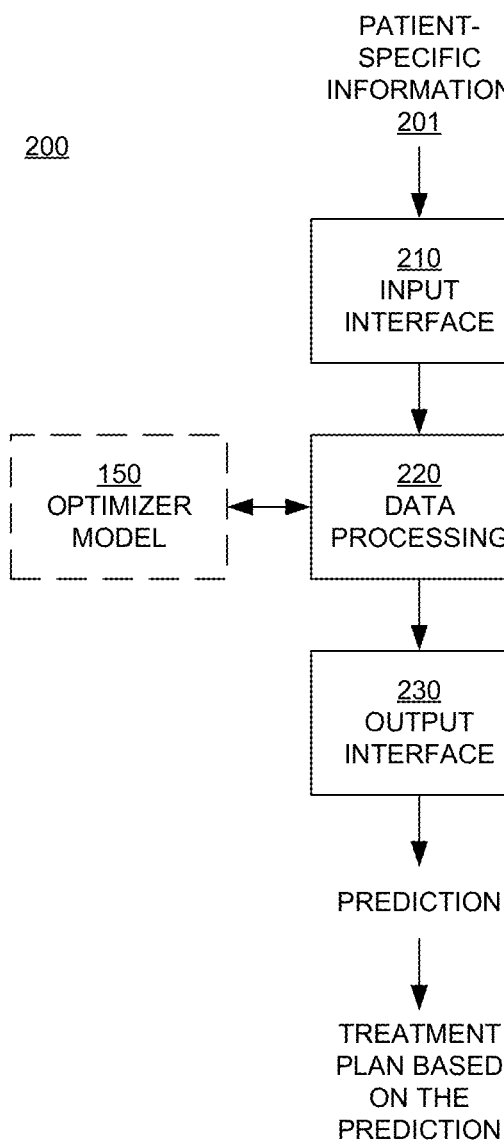
FIG. 2 is a block diagram illustrating an example of an automated radiation therapy treatment planning system in embodiments according to the present invention.

FIG. 2 is a block diagram of an exemplary automated radiation therapy treatment planning system 200 in accordance with one embodiment. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computer system 100 (FIG. 1).

In the example of FIG. 2, the patient-specific information is provided to and processed by the optimizer model 150. The optimizer model 150 yields a prediction result. A treatment plan based on the prediction result can then be generated.

Figure 3:
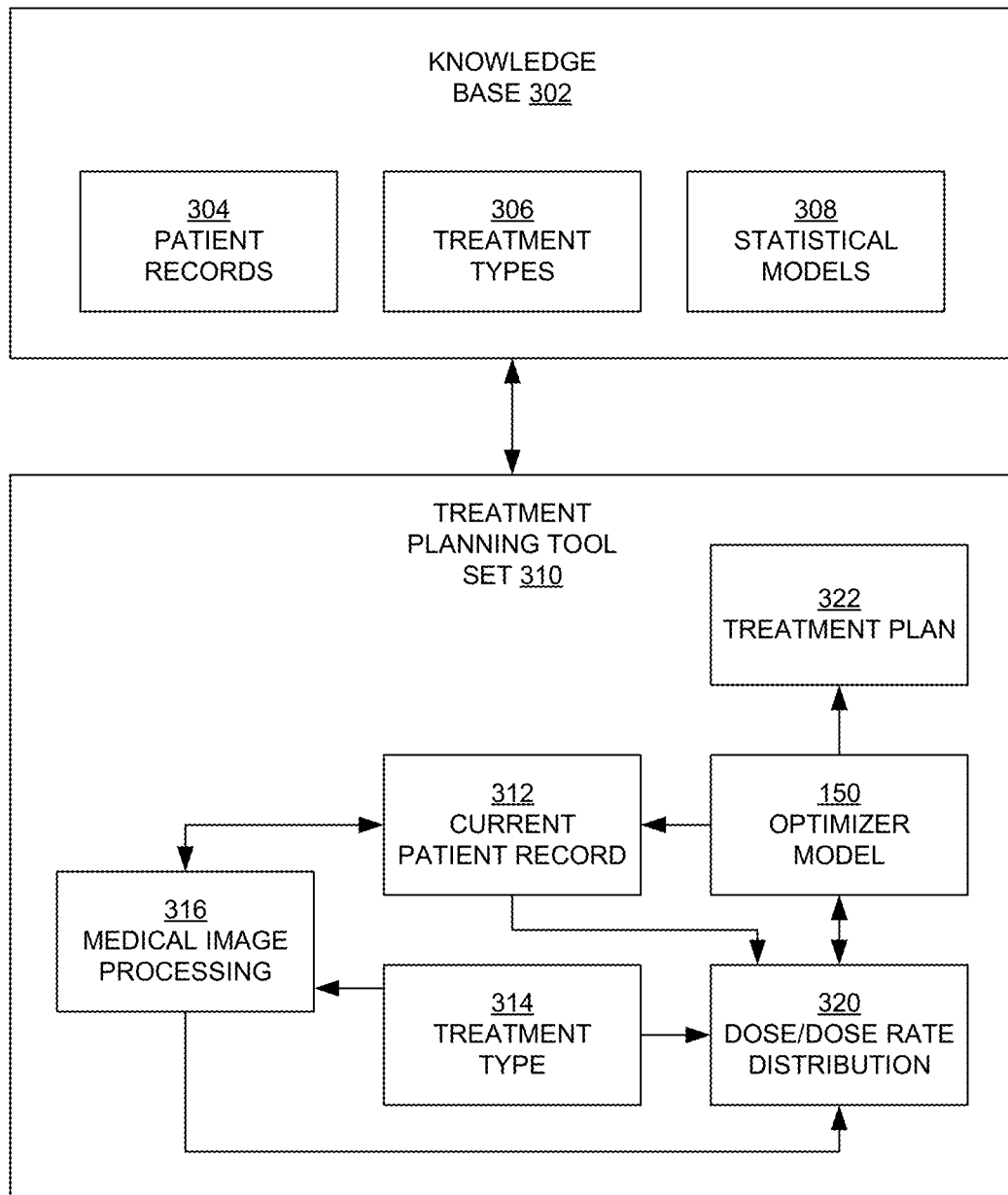
FIG. 3 illustrates an example of a knowledge-based planning system in an embodiment according to the present invention.

FIG. 3 is a block diagram of an exemplary knowledge-based planning system 300 in accordance with one embodiment. In the example of FIG. 3, the system 300 includes a knowledge base 302 and a treatment planning tool set 310. The knowledge base 302 includes patient records 304 (e.g., radiation treatment plans, etc.), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322. The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. Patient outcomes, which can include normal tissue complication probability as a function of dose rate and patient-specific treatment-type outcomes (e.g., local recurrent failure, and overall survival as a function of a dose rate-volume histogram (FIG. 7A) and an irradiation time-volume histogram (FIG. 7D)), can be included in the treatment planning process. The medical image processing module 316 provides automatic contouring and automatic segmentation of two-dimensional cross-sectional slides (e.g., from any imaging modality such as computed tomography (CT), positron emission tomography-CT, magnetic resonance imaging, and ultrasound) to form a three-dimensional (3D) image using the medical images in the current patient record 312. Dose distribution maps and dose rate distribution maps are calculated by the dose and dose rate distribution module 320, which may utilize the optimizer model 150.

In one embodiment, the optimizer model 150 uses a dose prediction model to provide, for example, a 3D dose distribution, fluences, and dose rates, and associated dose-volume histograms and dose rate-volume histograms.

The discussion to follow refers to beams, target volumes, doses, dose rates, and other elements or values. The discussion below is in the context of modeled elements and calculated values in the treatment planning tool set 310 and the optimizer model 150 (FIG. 3), unless otherwise noted or made clear in the discussion.

Figure 4:
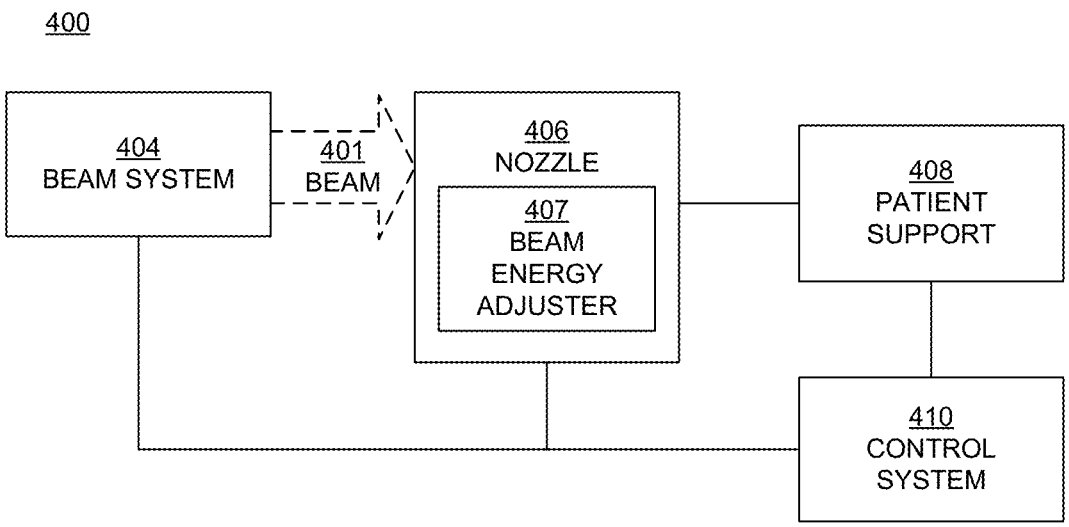
FIG. 4 is a block diagram showing an example of selected components of a radiation therapy system upon which an embodiment according to the present invention can be implemented.

FIG. 4 is a block diagram showing selected components of exemplary radiation therapy system 400 in accordance with one embodiment. In the example of FIG. 4, the system 400 includes a beam system 404 and a nozzle 406.

The beam system 404 generates and transports a beam 401. The beam 401 can be a proton beam, electron beam, photon beam, ion beam, or atom nuclei beam (e.g., carbon, helium, and lithium). In one embodiment, depending on the type of beam, the beam system 404 includes components that direct (e.g., bend, steer, or guide) the beam system in a direction toward and into a nozzle 406. The radiation therapy system can include a multileaf collimator (MLCs); each MLC leaf can be independently moved back-and-forth by the control system 410 to dynamically shape an aperture through which the beam can pass, to block or not block portions of the beam and thereby control beam shape and exposure time. The beam system 404 can also include components that are used to adjust (e.g., reduce) the beam energy entering the nozzle 406.

The nozzle 406 is used to aim the beam toward various locations (e.g., a target volume, etc.) within an object (e.g., a patient, etc.) supported on the patient support device 408 (e.g., a chair or table, etc.) in a treatment room. A target volume can be an organ, a portion of an organ (e.g., a volume or region within the organ, etc.), a tumor, diseased tissue, a patient outline, and so on. A target volume can include both unhealthy tissue (e.g., a tumor, etc.) and healthy tissue. The nozzle 406 can be mounted on or a part of a gantry that can be moved relative to the patient support device 408, which can also be moveable. In embodiments, the beam system 404 is also mounted on or is a part of the gantry. In another embodiment, the beam system is separate from (but in communication with) the gantry.

The control system 410 of FIG. 4 receives and implements a prescribed radiation treatment plan. In one embodiment, the control system 410 includes a computer system having a processor, memory, an input device (e.g., a keyboard), and perhaps a display in well-known fashion. The control system 410 can receive data regarding operation of the system 400. The control system 410 can control parameters of the beam system 404, nozzle 406, and patient support device 408, including parameters such as the energy, intensity, direction, size, and shape of the beam, according to data it receives and according to the prescribed radiation treatment plan.

As noted above, the beam entering the nozzle 406 has a specified energy. Thus, the nozzle 406 can include a component that affects (e.g., decrease, modulate) the energy of the beam. The term "beam energy adjuster" is used herein as a general term for a component or components that affect the energy of the beam, in order to control the range of the beam (e.g., the extent that the beam penetrates into a target), to control the dose delivered by the beam, and to control the depth dose curve of the beam, depending on the type of beam. For example, for a proton beam or an ion beam that has a Bragg peak, the beam energy adjuster can control the location of the Bragg peak in the target volume. In various embodiments, the beam energy adjuster 407 includes a range modulator, a range shifter, or both a range modulator and a range shifter.

Presented dose and dose rate approaches can be utilized with various types of radiation treatment processes. The radiation treatment processes can include radiation therapy techniques in which the intensity of the particle beam is either constant or modulated across a field of delivery (e.g., intensity modulated radiation therapy (IMRT), intensity modulated particle therapy (IMPT), beam intensity is varied across each treatment region or target volume in a patient, etc.). Presented dose and dose rate approaches can be used in spatially fractionated radiation therapy including high-dose spatially fractionated grid radiation therapy and micro-beam radiation therapy.

Figure 5:
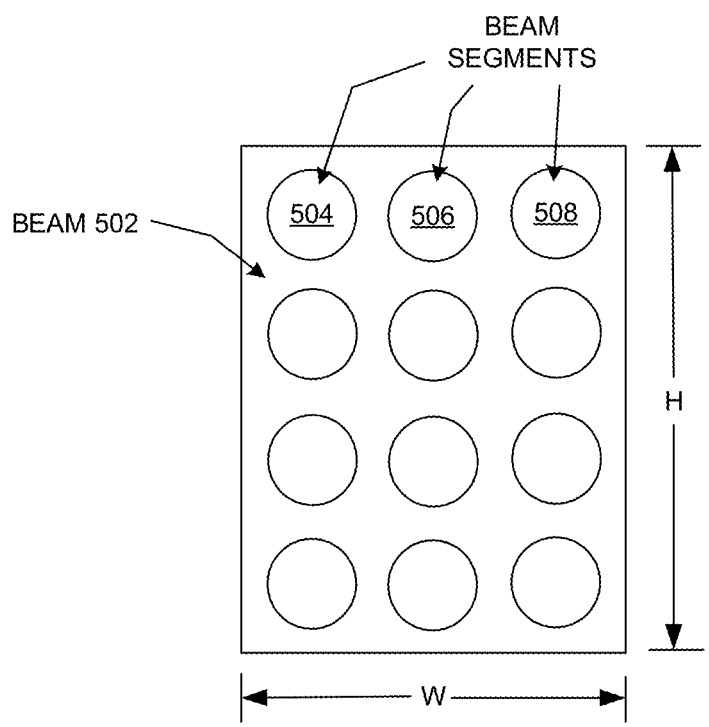
FIG. 5 illustrates an example of a beam's eye view of a beam in an embodiment according to the invention.

FIG. 5 illustrates a beam's eye view (BEV) of a beam 502 in accordance with one embodiment. That is, FIG. 5 illustrates a cross-section of a beam. The beam 502 is illustrated as being rectangular in shape having a height H and width W. However, the invention is not so limited, and the beam 502 can have virtually any regular or irregular cross-sectional (e.g., BEV) shape. For example, the shape of the beam 502 can be defined using an MLC that blocks a portion or portions of the beam. Different beams can have different shapes.

In the FIG. 5 embodiment, the beam 502 includes a number of beam segments or beamlets (that also can be referred to as spots) exemplified by beam segments 504, 506, and 508. A maximum energy (e.g., 80 MeV) is specified for the beam 502, and an energy level is defined for each of the beam segments as a percentage or fraction of the maximum energy. In essence, each of the beam segments is weighted in terms of its energy level; some beam segments are weighted to have a higher energy level than other beam segments. By weighting the energy per beam segment, in effect the intensity of each beam segment is also weighted. The defined energy level or intensity can be realized for each beam segment using the beam energy adjuster 407 of FIG. 4.

Each beam segment can deliver a relatively high dose rate (a relatively high dose in a relatively short period of time). For example, each beam segment can deliver at least 40 grays in less than or equal to one second (e.g., 40 Gy/s, etc.), and can deliver as much as 20 Gy to 50 Gy or 100 Gy or more in less than or equal to one second.

In operation, in one embodiment, the beam segments are delivered sequentially. For example, the beam segment 504 is delivered to the target volume (turned on) and then turned off, then the beam segment 506 is turned on then off, then the beam segment 508 is turned on then off, and so on. Each beam segment can be turned on for only a fraction of a second (e.g., on the order of milliseconds, on the order of seconds, etc.). In one embodiment, a beam is not switched on and off when moving from one to the next beam position. In one exemplary implementation, for spot distances that are customized to be larger than a definable threshold (e.g., spot distances of 10 mm or larger, etc.) the beam is turned off in between spots.

Figure 6A:
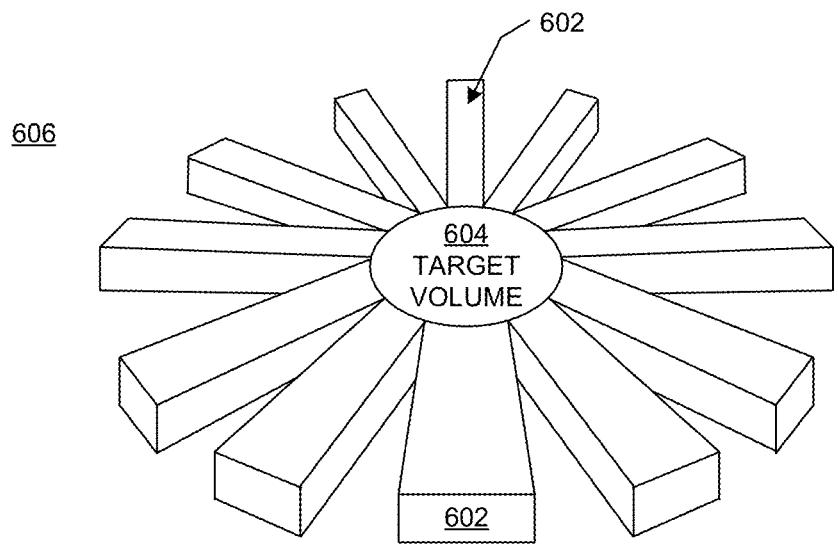
FIG. 6A illustrates a perspective view of an example of a beam geometry in an embodiment according to the invention.

FIG. 6A illustrates an exemplary perspective view of an example of a beam geometry in accordance with one embodiment. In the example of FIG. 6A, the beams (exemplified by beam 602) are in the same plane. The beams can be proton beams, electron beams, photon beams, ion beams, or atom nuclei beams. Each beam can deliver a relatively high dose rate (a relatively high dose in a relatively short period of time). For example, in embodiments, each beam can deliver doses sufficient for FLASH RT (e.g., at least 40 Gy in less than or equal to one second (e.g., 40 Gy/s, etc.), and as much as 20 Gy to 50 Gy or 100 Gy or more in less than or equal to one second). Each beam can include a beam segment or beamlets. In this example, the beams' paths overlap only within the target volume 604, and do not overlap outside the target volume in the surrounding tissue 606.

In the example of FIG. 6A, the beam 602 (for example) is illustrated as passing completely through the target volume 604. For beams that have a Bragg peak (e.g., proton beams and ion beams), the ranges of the beams can be controlled so that the beam does not pass completely through the target volume. In one embodiment, for FLASH transmission therapy with protons the proton energy is selected such that a Bragg Peak is neither located in the target volume nor in the patient at all.

Although multiple beams are shown in FIG. 6A, this does not mean that all beams are necessarily delivered at the same time or in overlapping time periods, although they can be.

Figure 6B:
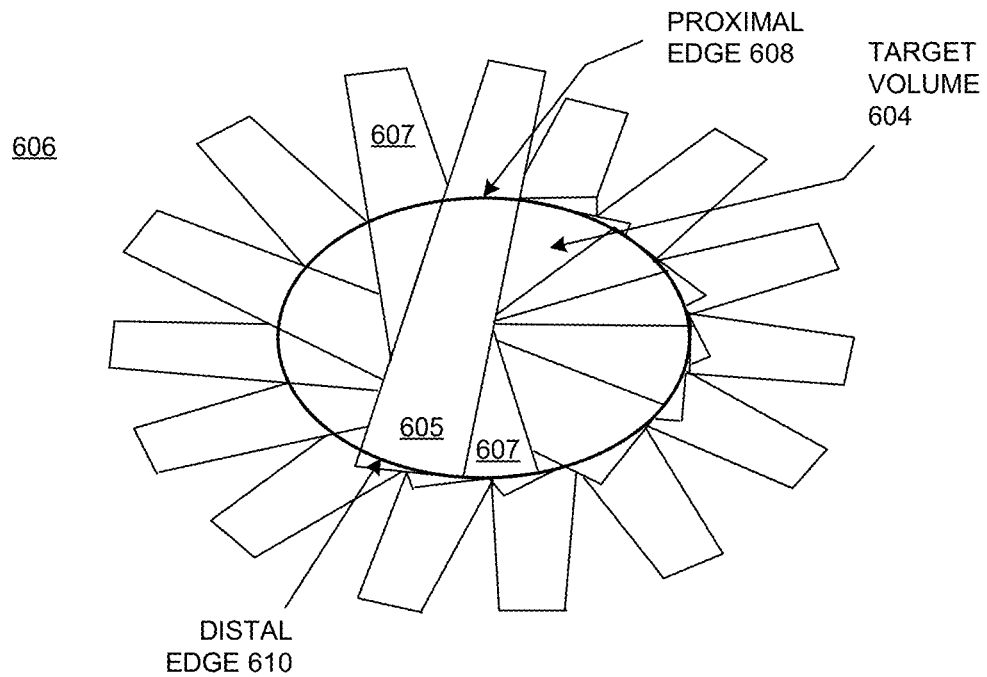
FIG. 6B illustrates a cross-sectional view of an example of a beam geometry in an embodiment according to the invention.

FIG. 6B illustrates a cross-sectional view of an example of a beam geometry in accordance with one embodiment. In this example, the beams (exemplified by beams 605 and 607) overlap only within the target volume and are in the same plane. The figure depicts the beams in overlapping fashion to demonstrate that each portion of the target volume 604 receives a dose of radiation. The beams can be proton beams, electron beams, photon beams, ion beams, or atom nuclei beams. In the example of FIG. 6B, the beams are illustrated as not extending beyond the distal edge of the target volume 604 (as would be the case for proton or ion beams, for example); however, the invention is not so limited. In one embodiment, transmission fields can be used in FLASH applications. Each beam can deliver a relatively high dose in a relatively short period of time. For example, each beam can deliver dose rates sufficient for FLASH RT.

Figure 6C:
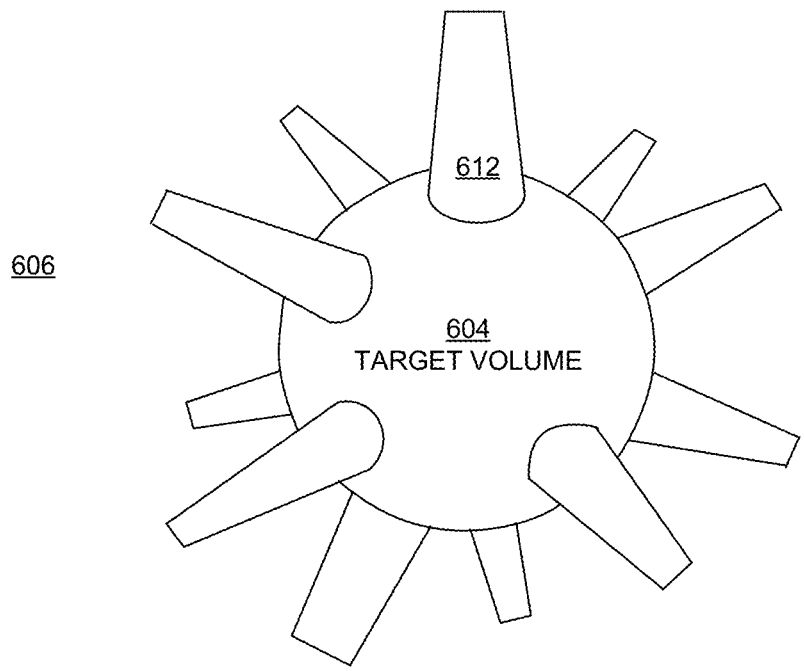
FIG. 6C illustrates a perspective view of an example of a beam geometry in an embodiment according to the invention.

FIG. 6C illustrates a perspective view of an example of a beam geometry in accordance with one embodiment. In the example of FIG. 6C, the beams (exemplified by beam 612) are in different planes. Each beam can include beam segment or beamlets. In this example, the beams' paths overlap only within the target volume 604, and do not overlap outside the target volume in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver dose rates sufficient for FLASH RT.

Figure 6D:
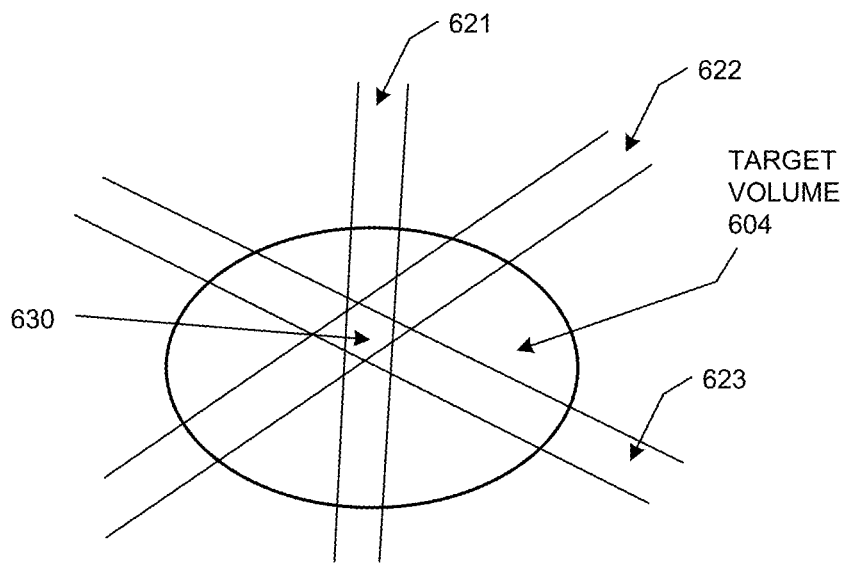
FIG. 6D illustrates a cross-sectional view of an example of a beam geometry in an embodiment according to the invention.

FIG. 6D illustrates a cross-sectional view of an example of a beam geometry in accordance with one embodiment. In this example, the beams (exemplified by beams 621, 622, and 623) overlap only within the target volume and are in the same plane. While three beams are illustrated, the invention is not so limited. As described herein, each beam can include a beam segment or beamlets. In this example, the beams' paths overlap only within the target volume 604, and do not overlap outside the target in the surrounding tissue 606. Although multiple beams are shown in the figure, all beams are not necessarily delivered at the same time or in overlapping time periods as mentioned above. The beams can be proton beams, electron beams, photon beams, ion beams, or atom nuclei beams. Each beam can deliver a relatively high dose in a relatively short period of time. For example, each beam can deliver dose rates sufficient for FLASH RT.

In the example of FIG. 6D, the beams 621, 622, and 623 intersect at the sub-volume 630, other sub-volumes in the target volume 604 receive doses from two of the beams, other sub-volumes in the target volume receive doses from only one of the beams, and yet other sub-volumes do not receive a dose. The directions and numbers of beam can be varied over a number of treatment sessions (that is, fractionated in time) so that a uniform dose is delivered across the target.

In one embodiment, a dose rate-volume histogram (which is different from, but can be used with, a dose-volume histogram) is generated for a target volume. The dose rate-volume histogram can be generated based on a proposed radiation treatment plan. The dose rate-volume histogram can be stored in computer system memory and used to generate a final radiation treatment plan that will be used to treat a patient. Values of parameters that can have an effect on dose rate can be adjusted until the dose rate-volume histogram satisfies objectives of or associated with treatment of the patient.

Figure 7A:
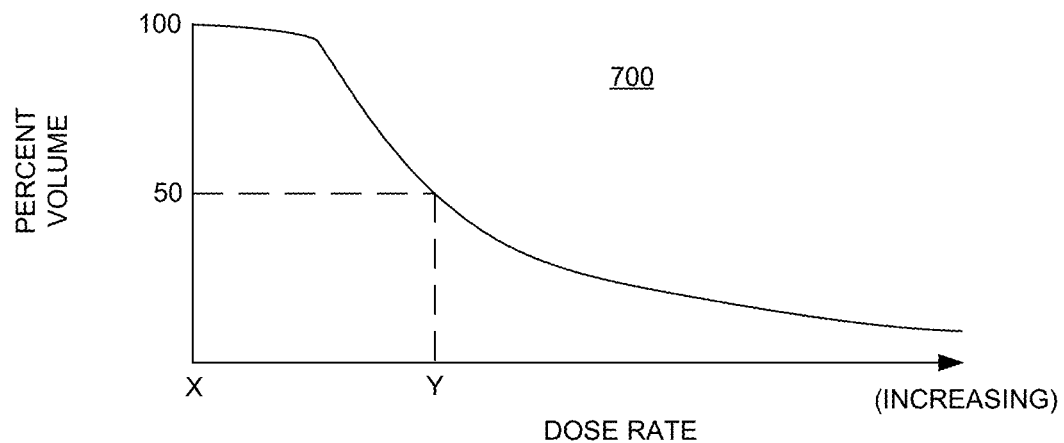
FIGS. 7A and 7B illustrate examples of dose rate-volume histograms in an embodiment according to the present invention

FIG. 7A illustrates an example of a dose rate-volume histogram 700 in an embodiment according to the present invention. The dose rate-volume histogram plots a dose rate-to-target volume frequency, distribution that summarizes the simulated dose rate distribution within a target volume of interest (e.g., the target volume 604 of FIGS. 6A-6D) that would result from a proposed radiation treatment plan. The simulated dose rate distribution can be determined using the optimizer model 150 of FIG. 1. The dose rate-volume histogram indicates dose rates and percentages of the target volume that receive the dose rates. For example, as shown in FIG. 7A, 100 percent of the target volume receives a dose rate of X, 50 percent of the target volume receives a dose rate of Y, and so on. The dose rate-volume histogram 700 can be displayed as or as part of a graphical user interface (GUI) (see the discussion of FIGS. 11, 12, and 13, below).

Figure 7B:
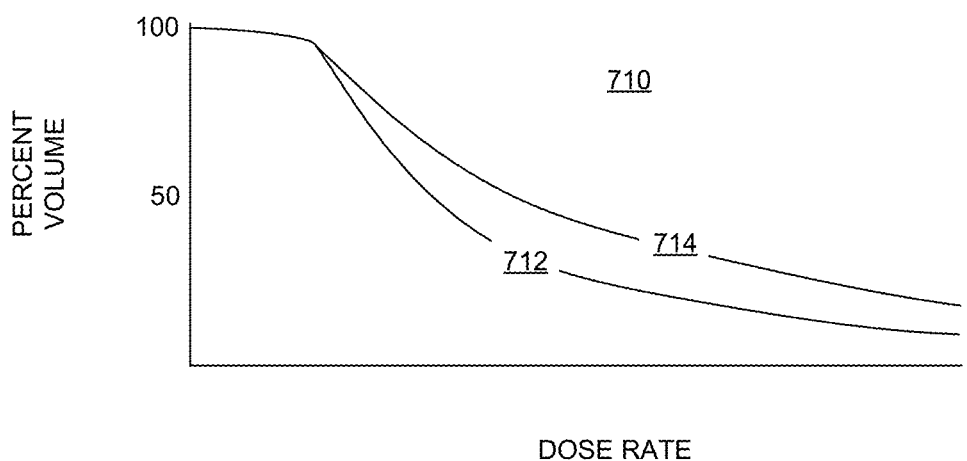
Figure 7C:
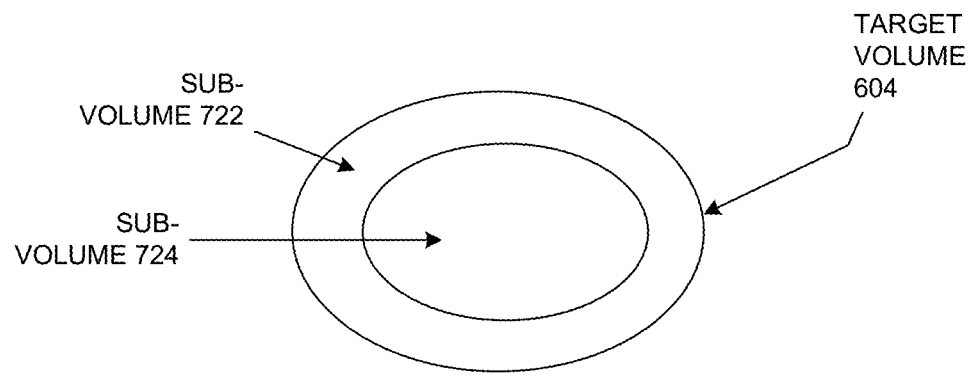
FIG. 7C illustrates example sub-volumes in a target volume in an embodiment according to the present invention.

The target volume 604 can include different organs, for example, or it can include both healthy tissue and unhealthy tissue (e.g., a tumor). Accordingly, with reference to FIGS. 7B and 7C, the dose rate-volume histogram 710 includes multiple curves 712 and 714, showing the simulated dose rate distribution for a first sub-volume 722 of the target volume (e.g., for one organ, or for the healthy tissue) and the simulated dose rate distribution for a second sub-volume 724 (e.g., for a second organ, or for the unhealthy tissue), respectively. More than two simulated dose rate distributions can be included in a dose rate-volume histogram. The dose rate-volume histogram 710 can be displayed as or as part of a GUI (see the discussion of FIGS. 11, 12, and 13, below).

The target volume 604 can be divided (virtually) into a number of voxels. A sub-volume can include a single voxel or multiple voxels.

In one embodiment, an irradiation time-volume histogram (which is different from, but can be used with, a dose-volume histogram and a dose rate-volume histogram) is generated for the target volume. The irradiation time-volume histogram can be stored in computer system memory and used to generate a radiation treatment plan, in combination with or in lieu of a dose-volume histogram and a dose rate-volume histogram.

Figure 7D:
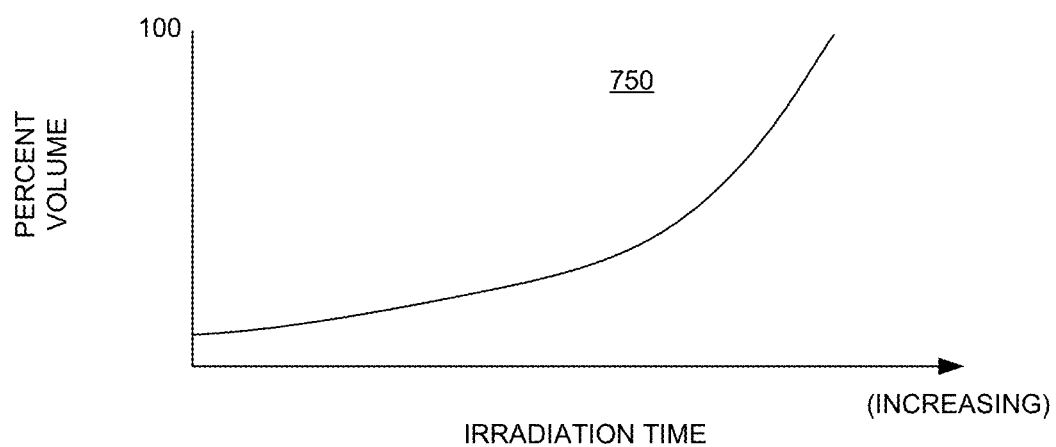
FIG. 7D illustrates an example of an irradiation time-volume histogram in an embodiment according to the present invention.

FIG. 7D illustrates an example of an irradiation time-volume histogram 750 in an embodiment according to the present invention. The irradiation time-volume histogram plots a cumulative irradiation time-to-target volume frequency distribution that summarizes the simulated irradiation time distribution within a target volume of interest (e.g., the target volume 604 of FIGS. 6A-6D) that would result from a proposed radiation treatment plan. The simulated irradiation time distribution can be determined using the optimizer model 150 of FIG. 1. The irradiation time-volume histogram indicates irradiation times (lengths of times) and percentages of the target volume that are irradiated for those lengths of time. The dose time-volume histogram 750 can be displayed as or as part of a GUI (see the discussion of FIGS. 11, 12, and 13, below).

Figure 8:
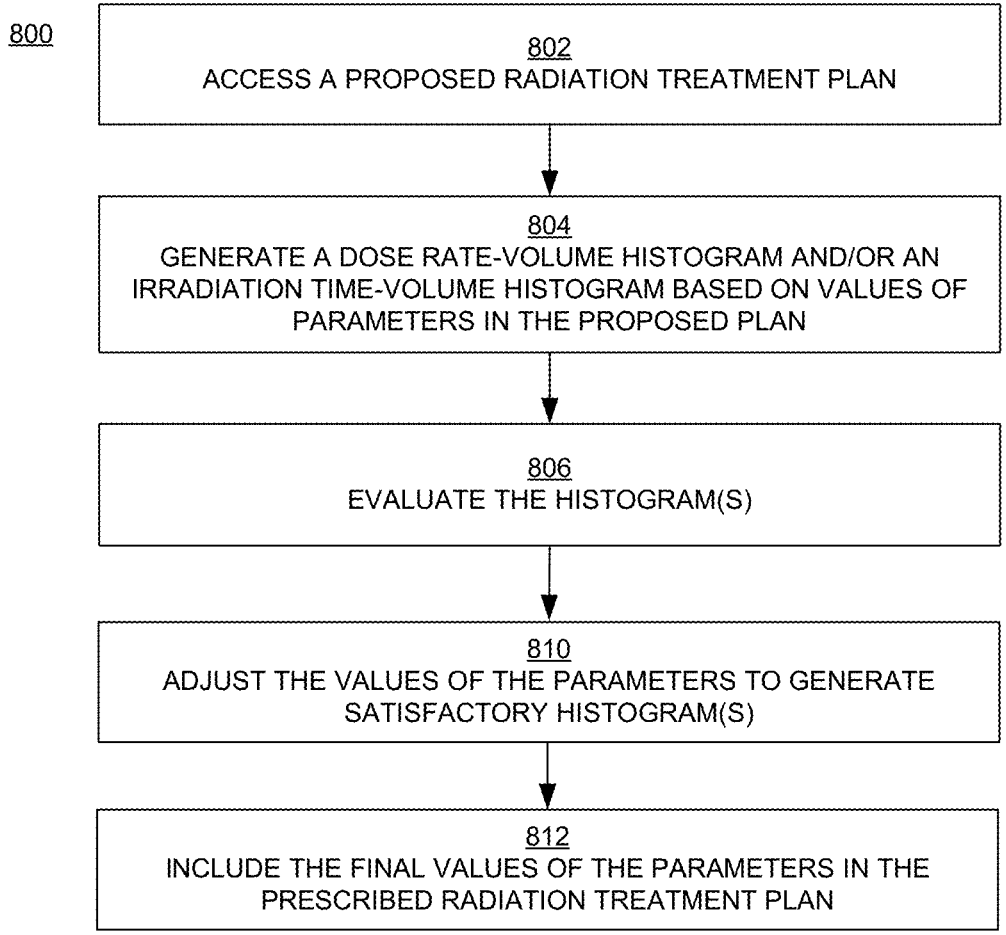
FIG. 8 is a flowchart of an example of computer-implemented operations for radiation treatment planning in embodiments according to the present invention.

FIG. 8 is a flowchart 800 of an example of computer-implemented operations for radiation treatment planning including generating a dose rate-volume histogram or an irradiation time-volume histogram in accordance with one embodiment. The flowchart 800 can be implemented as computer-executable instructions (e.g., the optimizer model 150 of FIG. 1) residing on some form of computer-readable storage medium (e.g., in memory of the computer system 100 of FIG. 1).

In block 802 of FIG. 8, a proposed radiation treatment plan is defined (e.g., using the optimizer model 150 of FIGS. 1 and 2), stored in a computer system memory, and accessed. The proposed radiation treatment plan includes values of parameters that can affect dose rate, as well as other parameters. The parameters that can affect dose rate include a number of irradiations of the target volume, a duration of each of the irradiations (irradiation times), and a dose deposited in each of the irradiations. The parameters can include directions of beams to be directed into the target volume, and beam energies for each of the beams. The parameters can also include a period of time during which the irradiations are applied (e.g., a number of irradiations are applied over a period of time such as an hour, with each irradiation in the period of time separated from the next by another period of time) and an interval of time between each period of irradiations (e.g., each hour-long period is separated from the next by a day). If the target volume is divided into sub-volumes or voxels, then the values of the parameters can be on a per-sub-volume or per-voxel basis (e.g., a value per sub-volume or voxel).

Appropriate dose threshold curve(s) (e.g., normal tissue sparing dose versus dose rate or irradiation time) can be utilized in the optimization model 150 (FIG. 3) to establish dose limits for radiation treatment planning. For example, the appropriate (e.g., tissue-dependent) dose threshold curve can be used to determine beam directions (gantry angles) and beam segment weights (FIG. 7A). That is, parameters that affect dose can be adjusted during radiation treatment planning so that the limits in the dose threshold curve are satisfied. The dose threshold curves can be tissue-dependent. For instance, the dose threshold curve for the lungs can be different from that for the brain.

Dose limits can include, but are not limited to: a maximum limit on irradiation time for each sub-volume (voxel) in the target (e.g., for each voxel of target tissue, treatment time less than x1 seconds); a maximum limit on irradiation time for each sub-volume (voxel) outside the target (e.g., for each voxel of normal tissue, treatment time less than x2 seconds; x1 and x2 can be the same or different); a minimum limit on dose rate for each sub-volume (voxel) in the target (e.g., for each voxel of target tissue, dose rate greater than y1 Gy/sec); and a minimum limit on dose rate for each sub-volume (voxel) outside the target (e.g., f or each voxel of normal tissue, dose rate greater than y2 Gy/sec; y1 and y2 may be the same or different). In general, the limits are intended to minimize the amount of time that normal tissue is irradiated.

In block 804, in an embodiment, a dose rate-volume histogram is generated based on the values of the parameters in the proposed radiation treatment plan. A dose rate can be determined per sub-volume or voxel. The average dose rate is the dose deposited in each irradiation divided by the sum of the durations of the irradiation, times the number of irradiations (e.g., number of fractions). The dose rate can be determined and recorded using a fine time index (e.g., time increments on the order of a millisecond); that is, for example, the dose to each sub-volume or voxel can be recorded for time increments on the order of per-millisecond per beam and per fraction. The dose rate per sub-volume or voxel can be calculated to include ray tracing (and Monte Carlo-like simulations), where each beam particle is tracked to determine the primary, secondary, etc., scatters for each particle to get a realistic voxel-based or sub-volume-based dose rate over the course of each irradiation.

In an embodiment, an irradiation time-volume histogram is generated. An irradiation time-volume histogram can be generated essentially in the same manner as that just described for generating a dose rate-volume histogram. Both a dose rate-volume histogram and an irradiation time-volume histogram, or only a dose rate-volume histogram, or only an irradiation time-volume histogram, can be generated, in addition to or in lieu of a dose-volume histogram.

In block 806, the dose rate-volume histogram and the irradiation time-volume histogram can be evaluated by determining whether or not objectives (e.g., clinical goals) that are specified for treatment of a patient are satisfied by the proposed radiation treatment plan. The clinical goals or objectives may be expressed in terms of a set of quality metrics, such as target homogeneity, critical organ sparing, and the like, with respective target values for the metrics. Another way to evaluate the dose rate-volume histogram and the irradiation time-volume histogram is a knowledge-based approach that incorporates and reflects present best practices gathered from multiple previous, similar treatments of other patients. Yet another way to assist the planner is to use a multi-criteria optimization (MCO) approach for treatment planning. Pareto surface navigation is an MCO technique that facilitates exploration of the tradeoffs between clinical goals. For a given set of clinical goals, a treatment plan is considered to be Pareto optimal if it satisfies the goals and none of the metrics can be improved without worsening at least one of the other metrics.

As mentioned above, for FLASH RT, dose rates of at least 40 Gy in less than or equal to one second (e.g., 40 Gy/s, etc.), and as much as 20 Gy to 50 Gy or 100 Gy or more in less than or equal to one second, may be used. Thus, another way to evaluate a dose rate-volume histogram is to define a dose rate threshold value (e.g., a minimum dose rate) based on the FLASH RT dose rates, and to also specify a target volume percentage threshold value for dose rate. A dose rate-volume histogram can be evaluated by determining whether the percentage of the target volume that receives a dose rate above the dose rate threshold value satisfies the percentage threshold value.

Another way to evaluate an irradiation time-volume histogram is to define an irradiation time threshold value or values (e.g., a maximum limit on irradiation time for each sub-volume or voxel inside the target volume and a maximum limit on irradiation time for each sub-volume or voxel outside the target volume), and to also specify a target volume percentage threshold value or values for irradiation time inside and outside the target volume. An irradiation time-volume histogram can be evaluated by determining whether the percentage of the tissue inside the target volume that is irradiated for less than the corresponding irradiation time threshold value satisfies the corresponding percentage threshold value, and by similarly determining whether the percentage of the tissue outside the target volume that is irradiated for less than the corresponding irradiation time threshold value satisfies the corresponding percentage threshold value.

In block 810 of FIG. 8, some or all of the parameter values for the proposed radiation treatment plan can be iteratively adjusted to generate different dose rate-volume histograms and the irradiation time-volume histograms, to determine a final set of parameter values that produce a histogram (or histograms) that results in a prescribed (final) radiation treatment plan that best satisfies the objectives (clinical goals) for treatment of the patient or that satisfies the threshold values described above.

In block 812, the final set of parameter values is then included in the prescribed radiation treatment plan used to treat the patient.

Generally speaking, embodiments according to the invention optimize a radiation treatment plan based on dose rate and irradiation time. This is not to say that treatment plan optimization is based solely on dose rate and irradiation time. For example, a dose-volume histogram can be used in conjunction with a dose rate-volume histogram and irradiation time-volume histogram when developing a radiation treatment plan.

Figure 9:
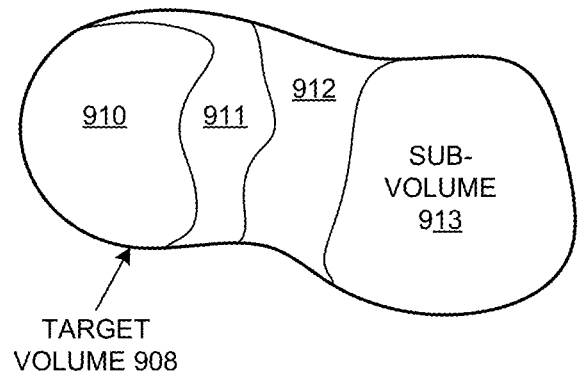
FIG. 9 is another illustration of example sub-volumes in a target volume in an embodiment according to the present invention.

As indicated previously (e.g., FIG. 7C, etc.) a target volume can include sub-volumes. It is appreciated that target volumes and sub-volumes can have various configurations. FIG. 9 is another illustration of example sub-volumes in a target volume in an embodiment according to the present invention. Target volume 908 includes sub-volumes 910, 911, 912, and 913.

Figure 10:
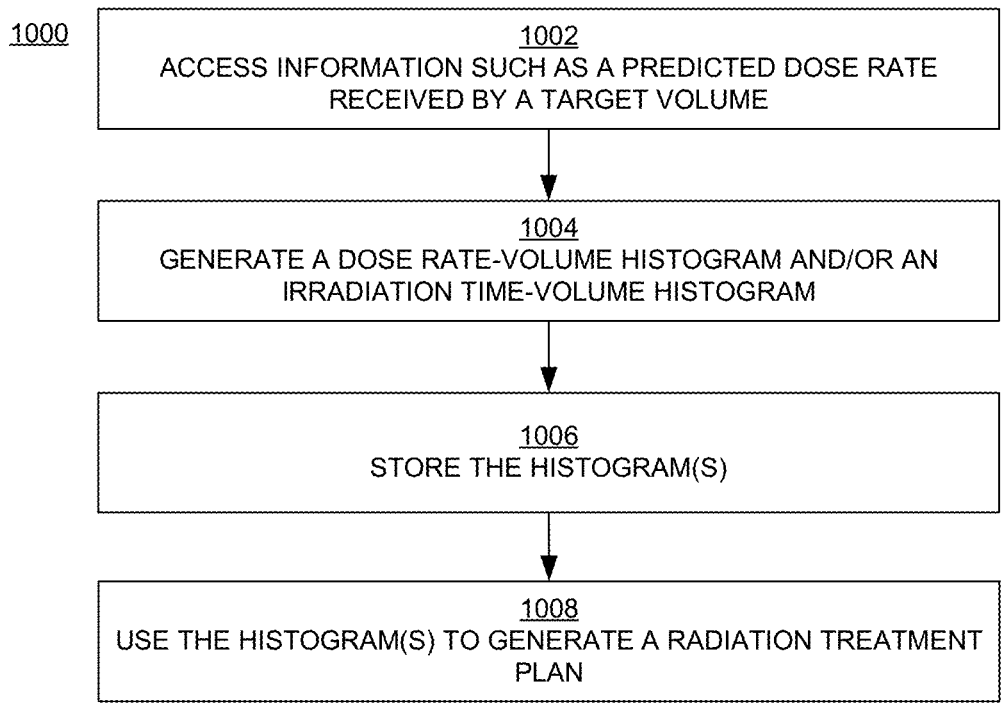
FIG. 10 is a flowchart of an example of computer-implemented operations for radiation treatment planning in an embodiment according to the present invention.

FIG. 10 is a flowchart 1000 of an example of computer-implemented operations for generating a dose rate-volume histogram in in accordance with one embodiment. The flowchart 1000 can be implemented as computer-executable instructions (e.g., the optimizer model 150 of FIG. 1) residing on some form of computer-readable storage medium (e.g., memory of the computer system 100 of FIG. 1).

In block 1002 of FIG. 10, information in computer system memory is accessed. The information includes a dose rate received by a target volume per sub-volume or voxel, determined using a dose prediction model implemented with the optimizer model 150 (FIG. 1). The information also can include irradiation time (duration) per sub-volume or voxel.

In block 1004 of FIG. 10, a dose rate-volume histogram and an irradiation time-volume histogram are/is generated for the target volume, as previously described herein (e.g., with reference to FIG. 8).

In block 1006 of FIG. 10, histograms that are generated are stored in computer system memory.

In block 1008, the dose rate-volume histogram and the irradiation time-volume histogram are/is used to generate a radiation treatment plan for treating the target volume.

Graphical User Interface for Radiation Treatment Planning

Figure 11:
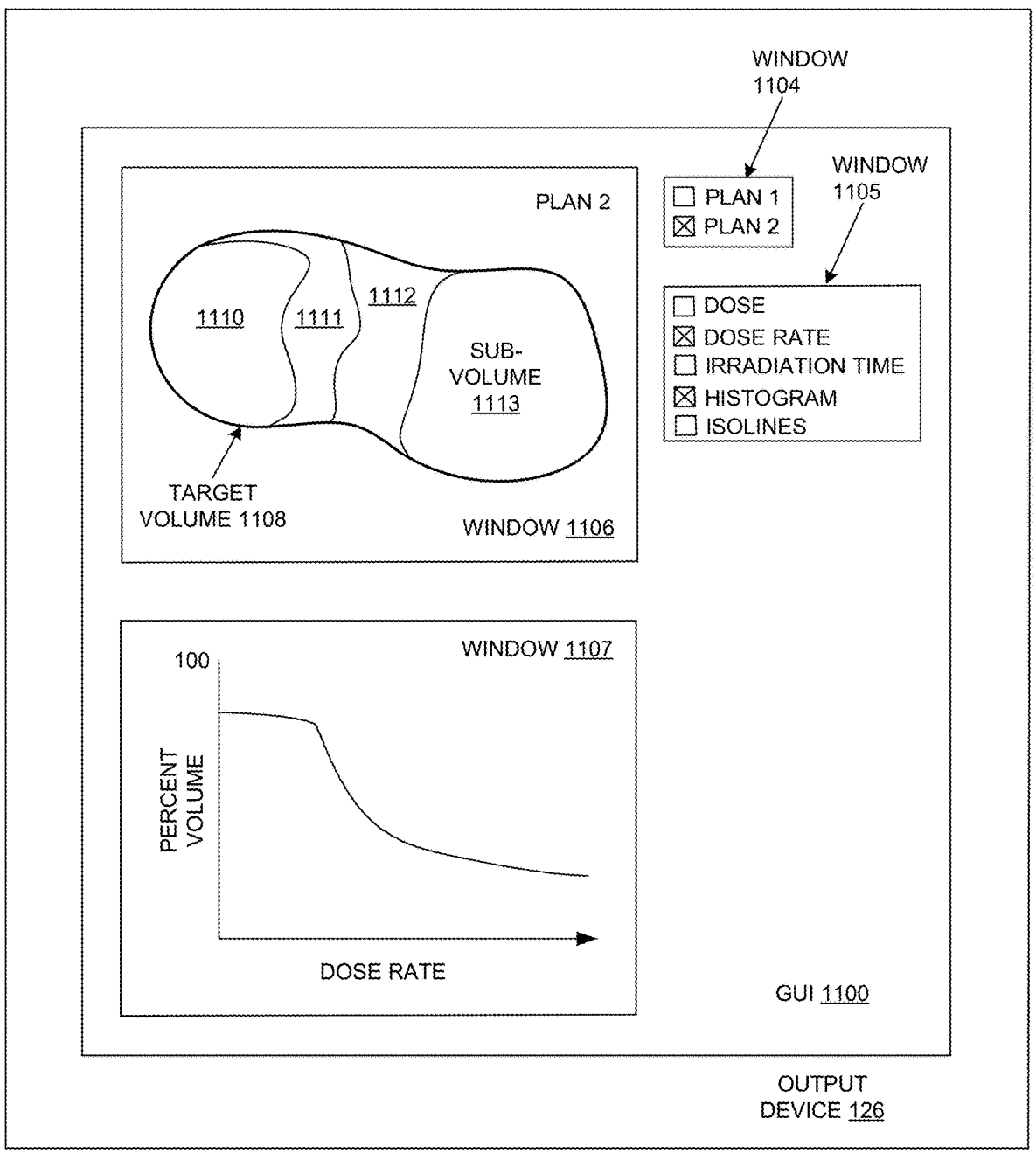
FIG. 11 illustrates an example of a graphical user interface (GUI) that can be used to display information associated with a radiation treatment plan in an embodiment according to the present invention.

FIG. 11 illustrates an example of a GUI 1100 that can be used to display information associated with a radiation treatment plan in accordance with one embodiment. The GUI 1100 can be implemented using computer-executable instructions (e.g., the optimizer model 150 of FIG. 1) residing on some form of computer-readable storage medium (e.g., memory of the computer system 100 of FIG. 1), and can be displayed on the output device 126 of the computer system.

In the example of FIG. 11, the GUI includes four windows 1104, 1105, 1106, and 1107, but the invention is not so limited. In this example, the window 1104 includes a menu or listing of different proposed radiation treatment plans (e.g., plan 1 and plan 2). If, for example, plan 2 is selected, then information associated with that plan is displayed in the windows 1106 and 1107.

In the FIG. 11 example, the window 1105 includes a menu or listing of types of information that can be presented in the GUI 1100. The types of information may include, but are not limited to, dose, dose rate, and irradiation time.

In this example, the window 1106 displays a representation of a target volume 1108. It is appreciated the representation of a target volume can have different configurations (e.g., similar to target volume 604, 908, etc.). The representation can be two-dimensional, representing a cross-sectional slice of the target volume 1108, or it can be a virtual three-dimensional representation of the target volume.

In the FIG. 11 example, the target volume 1108 includes four sub-volumes 1110, 1111, 1112, and 1113 (1110-1113). In an embodiment, the sub-volumes 1110-1113 may represent different regions (e.g., healthy tissue and non-healthy tissue or tumor) within a patient, different organs within a patient, or different regions within tissue or an organ, for example. The sub-volumes 1110-1113 can be any shape. In an embodiment, a sub-volume may be a single voxel or a set of voxels within a region or organ.

In embodiments, a value of an attribute is associated with each of the sub-volumes 1110-1113. The attribute can be color, pattern, gray-scale, alphanumeric text, and brightness, or a combination. The value can be, for example, a particular color, a particular pattern, a level of gray-scale, a character or combination of characters, or a level of brightness. The value of the attribute for a sub-volume corresponds to, for example, the amount of the dose rate, the amount of dose, or the irradiation time received by or associated with the sub-volume according to the selected radiation plan (e.g., plan 2). For example, one color value (e.g., blue) may correspond to a dose rate between zero and a first threshold, a second color value (e.g., green) may correspond to a dose rate between the first threshold and a second threshold, and so on.

As discussed above, the dose rate received by a sub-volume can be determined using parameters including the number of irradiations of the sub-volume, a duration of each of the irradiations, and a dose deposited in each of the irradiations. This type of information can also be presented in the GUI 1100. For example, the value of the attribute for a sub-volume can correspond to one of the parameters. Thus, for example, a first color value may correspond to a first number of irradiations, a second color value may correspond to a second number of irradiations, and so on.

The GUI 1100 can also be used to present information such as the directions of beams to be directed into each sub-volume, and beam energies for each of the beams.

In the example of FIG. 11, the window 1107 displays a selected histogram. For example, if dose rate is of interest, then the window 1107 can include a dose rate-volume histogram (e.g., the histograms 700 and 710 of FIGS. 7A and 7B). Alternatively, an irradiation time-volume histogram (e.g., the histogram 750 of FIG. 7D).

In embodiments, drop-down menus or other types of GUI elements (not shown) can be used to select and establish settings (e.g., attributes, thresholds, etc.) for the GUI 1100 and the type(s) of information to be displayed at any one time.

The GUI 1100 is not necessarily a static display. For example, the information presented in the GUI 1100 can be programmed to change over time to illustrate accumulated dose or dose rate versus time. Also, for example, the GUI 1100 can be programmed to present different cross-sectional slices of the target volume 1108 in sequence to provide a depth dimension to the two-dimensional representation, or to manipulate (e.g., rotate) the virtual three-dimensional representation so that it can be viewed from different perspectives.

FIGS. 12 and 13 are flowcharts 1200 and 1300, respectively, of examples of computer-implemented operations for generating a GUI (e.g., the GUI 1100 of FIG. 11) in accordance with one embodiment. The flowcharts 1200 and 1300 can be implemented as computer-executable instructions (e.g., the optimizer model 150 of FIG. 1) residing on some form of computer-readable storage medium (e.g., in memory of the computer system 100 of FIG. 1).

In block 1202 of FIG. 12, information in the computer system memory is accessed. In an embodiment, the information includes a dose rate received by each sub-volume of a target volume. The dose rate received by each sub-volume is determined as previously described herein. In an embodiment, the information includes an irradiation time per sub-volume.

In block 1204, a value of an attribute is associated with each sub-volume. In an embodiment, the value corresponds to an amount of the dose rate received by a respective sub-volume. The attribute can be, for example, color, pattern, gray-scale, alphanumeric text, brightness, or a combination of these attributes. The value can be, for example, a particular color, a particular pattern, a level of gray-scale, a character or combination of characters, or a level of brightness.

In block 1206, each sub-volume is rendered and displayed according to the value that corresponds to the sub-volume as described above.

In block 1302 of FIG. 13, in an embodiment, information that includes a dose rate received by a target volume is accessed from the memory of the computer system.

In block 1304, a histogram is generated for the target volume. The histogram may be a dose rate-volume histogram and an irradiation time-volume histogram as previously described herein.

In block 1306, the histogram is displayed in a GUI as described above.

While the operations in FIGS. 8, 10, 12, and 13 are presented as occurring in series and in a certain order, the present invention is not so limited. The operations may be performed in a different order and in parallel, and they may also be performed in an iterative manner. As noted above, because of the different parameters that need to be considered, the range of values for those parameters, the interrelationship of those parameters, the need for treatment plans to be effective yet minimize risk to the patient, and the need to generate high-quality treatment plans quickly, the use of the optimizer model 150 executing consistently on the computer system 100 (FIG. 1) for radiation treatment planning as disclosed herein is important.

Dose Rate Volume Histogram with Uncertainties.

As indicated above, one approach to deliver ultra-high dose rates (e.g., in scanned proton therapy, etc.) uses transmissions fields which consist of a single high energy layer. However, there are various uncertainties that can affect the actual dose rate finally experienced by an irradiated volume during treatment plan delivery. The uncertainty can be associated with potential variations associated with tolerances (e.g., radiation system/machine performance tolerance, patient characteristic tolerances, etc.) and set up issues (e.g., variation in initial system/machine set up, variation patient setup/position, etc.). The uncertainties can affect the actual dose rate finally experienced by an irradiated volume during treatment plan delivery. Radiation system performance tolerances can correspond to accelerator or machine-specific operations (e.g., beam current fluctuations, spot size variations, etc.). Uncertainties can also relate to other tolerance variations (e.g., changes in patient characteristics, weight, etc.). Setup variations or errors (e.g., patient location/orientation, initial machine settings/calibration, etc.) can also typically impact or influence the dose rate distribution. In one embodiment, individual tolerances (based on uncertainties/variations) of parameters impacting the dose rate are currently not considered for radiation treatment planning. Thus, in one exemplary implementation radiation treatment plans generated to meet a prescribed dose rate (beside other treatment plan prescription parameters) can typically achieve a planned dose rate within a dedicated tolerance during actual treatment delivery only. Dose rate conformity analysis as part of treatment plan quality evaluation can be essential for radiation treatment plans that include dose rate prescriptions. However, calculation, display, and visualization of dose rate distributions for a given set of uncertainty scenarios is not previously typically available in commercial radiation treatment planning.

In one embodiment, similar to dose volume histograms in radiotherapy described above, a histogram relating dose rate to tissue volume is calculated, displayed and visualized for different uncertainty scenarios, arising from tolerances in patient positioning and machine performance. For each uncertainty scenario, users (e.g., physicians, clinicians, technicians, etc.) can assess the proportion of irradiated volume (in absolute or relative numbers) receiving a user-selectable dose rate. Depending on the likelihoods of the analyzed uncertainty scenarios a decision can be made regarding the acceptability/robustness of treatment plan prescription parameters (e.g., dose, dose rate, etc.).

In one embodiment, an uncertainty parameter can be associated with a set of uncertainty scenarios and a plurality of DRVH graph curves can be generated in a histogram. In one exemplary implementation, a different one of the plurality of DRVH graph curves is created for respective ones of the multiple different uncertainty parameter values. The plurality of DRVH graph curves can form a DRVH band. In one embodiment, a combination of multiple different uncertainty parameters are associated with a set of multiple different uncertainty scenarios. Respective ones of the multiple different uncertainty parameters can be associated with a set of uncertainty scenarios. In one exemplary embodiment, histogram generation conditions can include multiple different scenarios, each scenario giving exponential rise to multiple different types of uncertainty parameters, with each type of uncertainty parameter giving rise exponentially to multiple different uncertainty parameter values. These conditions result in potential involvement of an immense number of different considerations/factors/values in the generation of histogram information. Thus, in addition to the numerous parameter and degrees of freedom in radiation beam generation (e.g., beam intensity, energy, angle of incidence, etc.) and different types of histograms (e.g., DRVH, etc.) previously described, inclusion of the numerous different possible uncertainty scenarios and values for a respective histogram further complicate and place consistent and effective generation of high-quality treatment plans further beyond the capability of a human as a practical matter without the aid of systems and methods presented herein.

Figure 14:
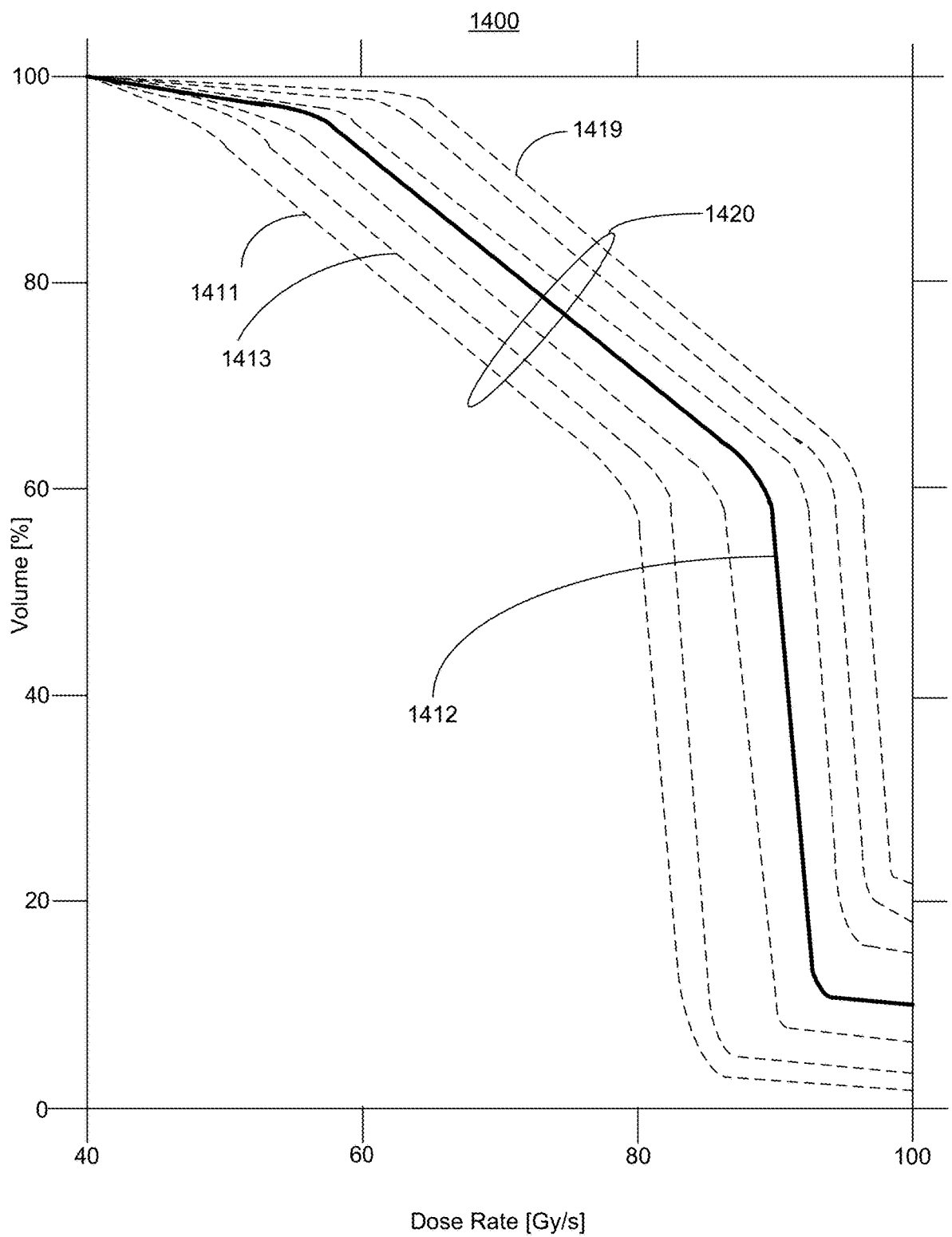
FIG. 14 is a graphical representation of an exemplary dose rate volume histogram in accordance with one embodiment.

FIG. 14 is a graphical representation of an exemplary dose rate volume histogram 1400 in accordance with one embodiment. In one exemplary implementation, the graphical representation is associated with a dose rate volume histogram (DRVH) for an ultra-dose rate (e.g., FLASH, etc.) treatment plan. The dose rate (e.g., Gy/s, etc.) is shown on the X axis and the amount or volume (e.g., percent, etc.) treated is shown on the Y axis. The DRVH graph curves are shown in dotted/dashed lines (e.g., 1411, 1412, 1419, etc.) corresponding to different uncertainty scenarios. In one embodiment, the solid line (e.g., 1412, etc.) indicates/highlights a selection of one of the dotted/dashed lines or rather one of the uncertainty scenarios. In one exemplary implementation, solid line 1412 was originally a dotted/dashed line (e.g., similar to dashes line 1411, etc.), but when selected became a solid line as shown in FIG. 14. If the uncertainty scenarios associated with graph curve 1413 is selected as active or one or interest, then graph curve line 1413 would change from dotted/dashed to solid and graph line 1412 would change from solid to dotted/dashed. In one exemplary implementation, a nominal DRVH curve is shown as a solid curve line. Collectively the dotted line curves and solid line curve can form a DRVH band (e.g., 1420, etc.). In one embodiment, such a DRVH band defines the region in which a graph curve for an actual treatment delivery would have a high probability of "lying" or being included in. If the band width is too large and a prescription parameter (e.g., the dose, the dose rate, etc.) does not fulfill or comply with the prescription, replanning might become necessary.

In one embodiment, a planning or prescription parameter (e.g., dose, dose rate, etc.) distribution calculated based on a radiation system or machine specific parameters by a treatment planning system represents only an estimate. In one exemplary implementation, the estimated prescription parameter distribution depends on a particular instance grabbed snapshot of radiation system or machine performance characteristics used as base data for a treatment planning machine. An actual prescription parameter distribution for other instances can deviate more or less depending on the tolerances for system/machine performance and patient setup errors. By neglecting such influencing factors, a prescribed parameter value might not be achieved during actual treatment delivery. Plan robustness with regard to prescribed parameters can be crucial, particularly in cases that have a radiation dose rate prescription (e.g., FLASH irradiations, etc.). With the help of histograms (e.g., DRH, DRVHs, etc.), the degree of robustness against different levels of uncertainties can be tested. In one exemplary implementation, if a plan is not sufficiently robust against uncertainty scenarios, the plan can be modified during treatment planning (e.g., before beginning actual treatment delivery, etc.).

Figure 15:
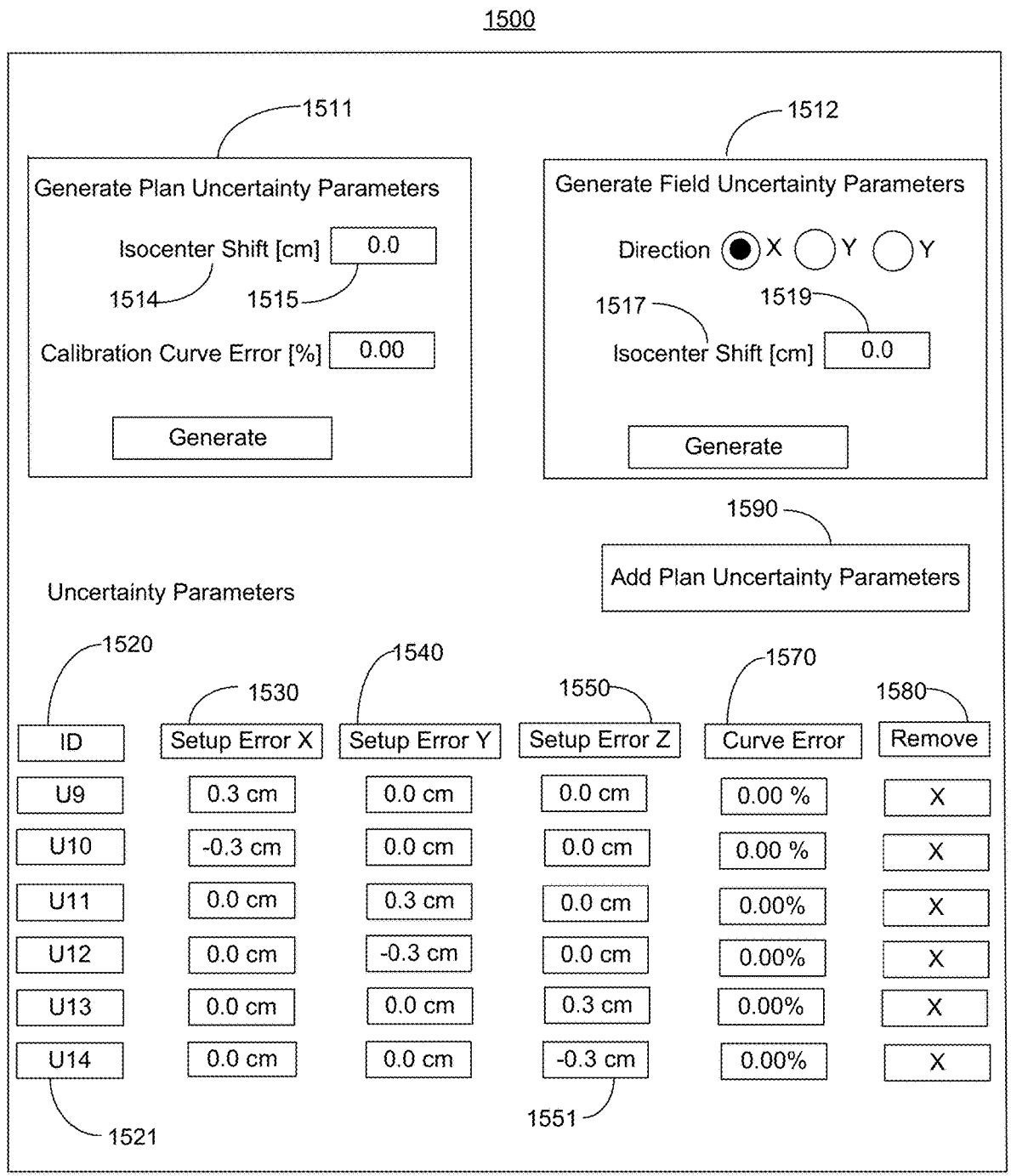
FIG. 15 is a block diagram of an uncertainty parameter input graphical user interface in accordance with one embodiment.

In one embodiment, the prescription parameter robustness evaluation is an integrated tool in the treatment planning system. In one exemplary implementation, a user can specify a set of uncertainty scenarios for which the prescription parameter distribution is recalculated. FIG. 15 is a block diagram of an uncertainty parameter input graphical user interface 1500 in accordance with one embodiment. Uncertainty parameter input graphical user interface 1500 can be utilized by a user to conveniently input and generate uncertainty parameters and values. Uncertainty parameter input graphical user interface 1500 includes various fillable fields. In one embodiment, the fillable fields can be utilized by a user to input information. In one exemplary implementation, an uncertainty parameter identifier (e.g., 1514, 1517, etc.) and corresponding uncertainty parameter fillable field (e.g., 1515, 1519, etc.) can be created.

Uncertainty parameter input graphical user interface 1500 includes a section 1511 to direct generation of plan uncertainty parameters and a section 1512 to direct generation of field uncertainty parameters. Section 1511 includes an isocenter shift fillable field, calibration curve error fillable field, and an generate initiation button. Section 1512 includes direction indicator fields, an isocenter shift fillable field, and an generate initiation button.

In one exemplary implementation, user defined uncertainties can be based on various factors (e.g., user experience, data coming from a machine log file analysis of dose rate uncertainties, etc.). In one embodiment, a patient positioning uncertainty in the X, Y, and Z directions is created resulting in six different scenarios (e.g., six different positions of the patient, etc.). In one exemplary implementation, a user can define the objectives that need to be achieved. The objectives can be equivalent to the problem that an optimizer is directed to solving.

Uncertainty parameter input graphical user interface 1500 can include a button to add plan uncertainty parameters. The plan uncertainty parameters can include an uncertainty scenario ID 1520, setup error in X direction 1530, setup error in Y direction 1540, setup error in Z direction 1550, curve error 1570, remove error 1580, and so on. The uncertainty parameters can have various fillable fields (e.g., 1521, 1551, etc.). Uncertainty parameter input graphical user interface 1500 can also include an add plan uncertainty parameter button 1590.

It is appreciated there can be various uncertainty parameters. In one embodiment, uncertainty parameters can be associated with performance/operation tolerances (e.g., radiation system and machine-specific operation tolerances and setup up scenarios such as patient setup, machine set up, and so on). In one exemplary proton therapy approach the uncertainty parameters may include: proton current fluctuations (e.g., $\Delta$IP=±1%, ±5%, etc.), setup errors (e.g., =$\Delta$X/$\Delta$Y/$\Delta$Z±1 mm, ±2 mm, et.), range uncertainties (e.g., 1%, 2%, 3%, etc.) including CT calibration curve uncertainties, uncertainties of the calculated spot times, uncertainties in the dose calculation, different transmission tables (depending on the treatment room), and so on.

In one embodiment, treatment planning including allowance/accommodation for various scenarios and corresponding uncertainties is implemented. In one embodiment, a treatment plan with allowances for uncertainties is generated similar to the treatment planning generation shown and described previously with reference back to knowledge-based planning system 300 in FIG. 3, flow chart 800 in FIG. 8, flowchart 1000 in FIG. 10, and so on. In one exemplary implementation, treatment plan generation includes optimization (e.g., similar to optimizer model 150, etc.) that further includes allowances/accommodations for various uncertainties. The optimizer model allowance/accommodation can include recalculation of prescription parameter distribution for various uncertainty scenarios.

Recalculated prescription parameter distribution for uncertainty scenarios can be presented in the form of a histogram (e.g., DVH, DRVH, etc.). In one exemplary implementation, the proportion of irradiated volume (in absolute or relative numbers) receiving a threshold dose rate $D_{th}$ and the dose rate received by (100-p) percent of the volume is displayed for uncertainty scenarios. The $D_{th}$ and p are variables that can be defined by the user. The histogram and DRVH parameters can be displayed for regions of interest (ROIs) selected by the user. The DRVH parameters and regions of interest can be similar to the DVH functionality set forth above, as well as other existing DVH functionality. In one embodiment, it is possible to define ROIs based on isodose levels to evaluate for example high dose regions. Thus, a user (e.g., physician, nurse, clinician, technician, etc.) can check whether prescribed parameter values are met for healthy tissue and relevant tissue/organs at risk (e.g., the target, tumor, etc.), respectively.

It is appreciated the potential results associated with various uncertainties can also be depicted in various types of histograms (e.g., a dose volume histogram (DVH), dose rate volume histogram (DVRH), etc.). FIG. 16 is a graphical representation of an objective definition input interface 1600 in accordance with one embodiment. Objective definition input interface 1600 can include an ID/type column, a volume expressed in centimeter cubed (cm$^3$) column, a volume expressed in percent (Vol %) column, a dose (Gy) column, an actual dose (Gy) column, a priority column, an RO column, a generalized equivalent uniform dose (gEUD) column, and so on. In one embodiment, a user can use objective definition input interface 1600 to assist with definition of treatment objectives that need to be achieved. In one exemplary implementation, the defined treatment objectives effectively become the basis for the problem the optimizer solves. In one exemplary implementation, objective definition input interface 1600 includes an Initial Clinical Target Volume (CTV0) section, a Brain Scan section, and a Continuous Positive Airway Pressure (CPAP) section. In one embodiment, objectives with a checkmark in the RO column are considered for the scenarios that are created and an optimizer tries to find a solution that meets the objectives for the scenarios.

Figure 17:
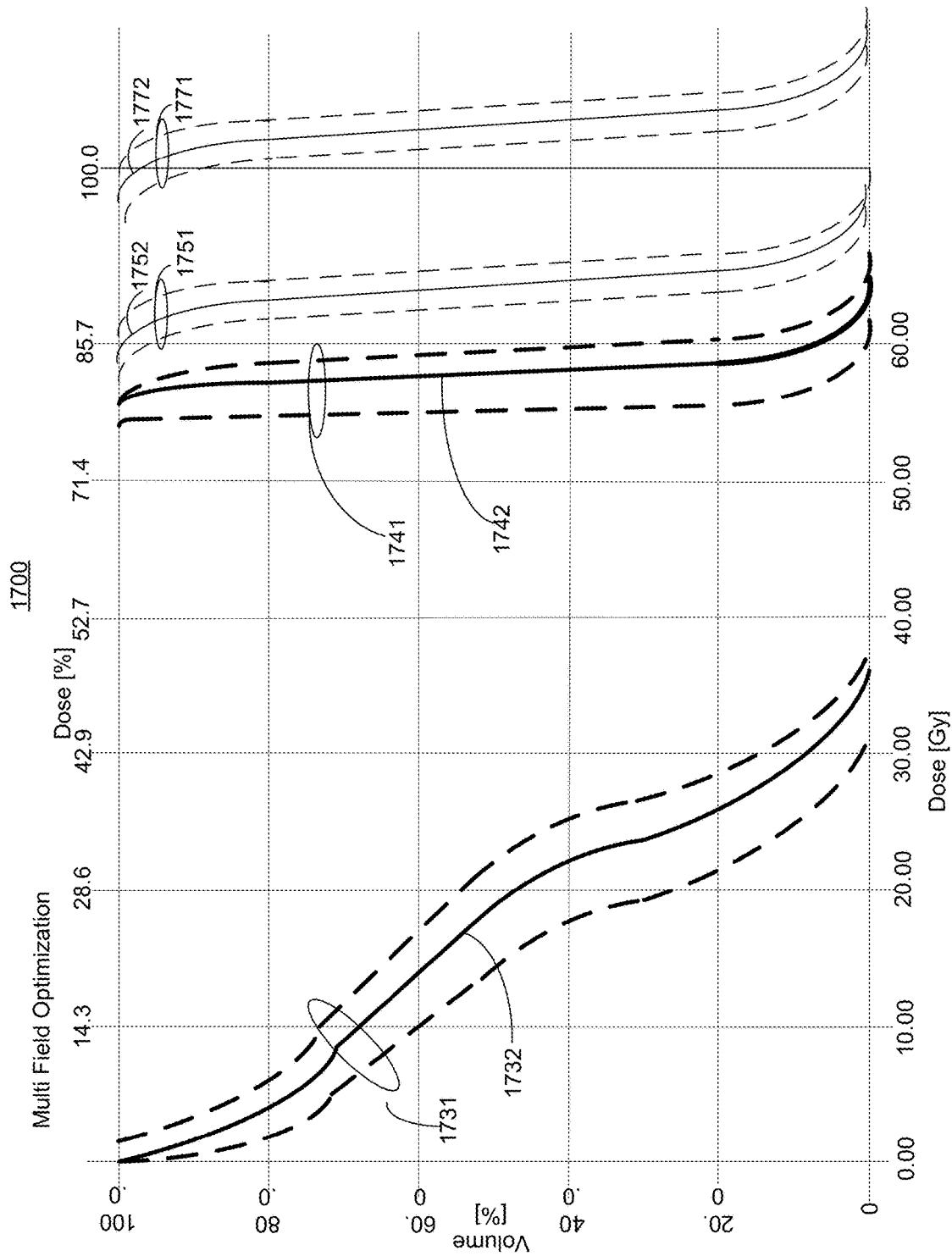
FIG. 17 is a graphical representation of a dose rate volume histogram in accordance with one embodiment.

FIG. 17 is a graphical representation 1700 of a dose rate volume histogram in accordance with one embodiment. In one exemplary implementation, a graphical representation 1700 is a multifield optimization dose volume histogram in accordance with one embodiment. In one embodiment, the volume is shown on the Y axis and the dose is shown on the X axis. In one exemplary implementation, the dose is expressed in radiation units on the bottom X axis and as a percentage on the top X axis. In one embodiment, there are three uncertainty scenarios.

In one exemplary implementation, graphical representation 1700 is similar to graphical representation 1400 except graphical representation 1700 includes multiple bands associated with a corresponding plurality of uncertainty scenarios. A first uncertainty scenario is associated with DVH band 1731 with multiple uncertainties in the scenario shown by the dotted lines which collectively form the DVH band 1731. A nominal DVH curve for DVH band 1731 is shown as a solid curve line 1732. A second uncertainty scenario is associated with DVH band 1741 with multiple uncertainties in the scenario shown by the dotted lines which collectively form the DVH band 1741. A nominal DVH curve for DVH band 1741 is shown as a solid curve line 1742. A third uncertainty scenario is associated with DVH band 1751 with multiple uncertainties in the scenario shown by the dotted lines which collectively form a DVH band 1751. A nominal DVH curve for DVH band 1751 is shown as a solid curve line 1752. A fourth uncertainty scenario is associated with DVH band 1771 with multiple uncertainties in the scenario shown by the dotted lines which collectively form a DVH band 1771. A nominal DVH curve for DVH band 1771 is shown as a solid curve line 1772.

In one embodiment, if an optimizer finds a perfect solution the Dose Volume Histogram (DVH) of each structure will be a single line. However, since there usually differences in multiple uncertainty scenarios that have impacts on the actual treatment results, a DVH for multiple uncertainty scenarios represented as a single graph curve line is usually not possible. Thus, a DVH for multiple scenarios is typically represented by a band of DVH curve graph lines. Different bands of DVH curve graph lines can be associated with different targets (e.g., tissue, tumors, etc.) or structures (e.g., lung, brain, etc.). In one embodiment, the bands 1741, 1751, and 1771 each represent a different structure. A shallow band means that the optimization finds a solution that provides a good result for the scenarios.

Figure 18:
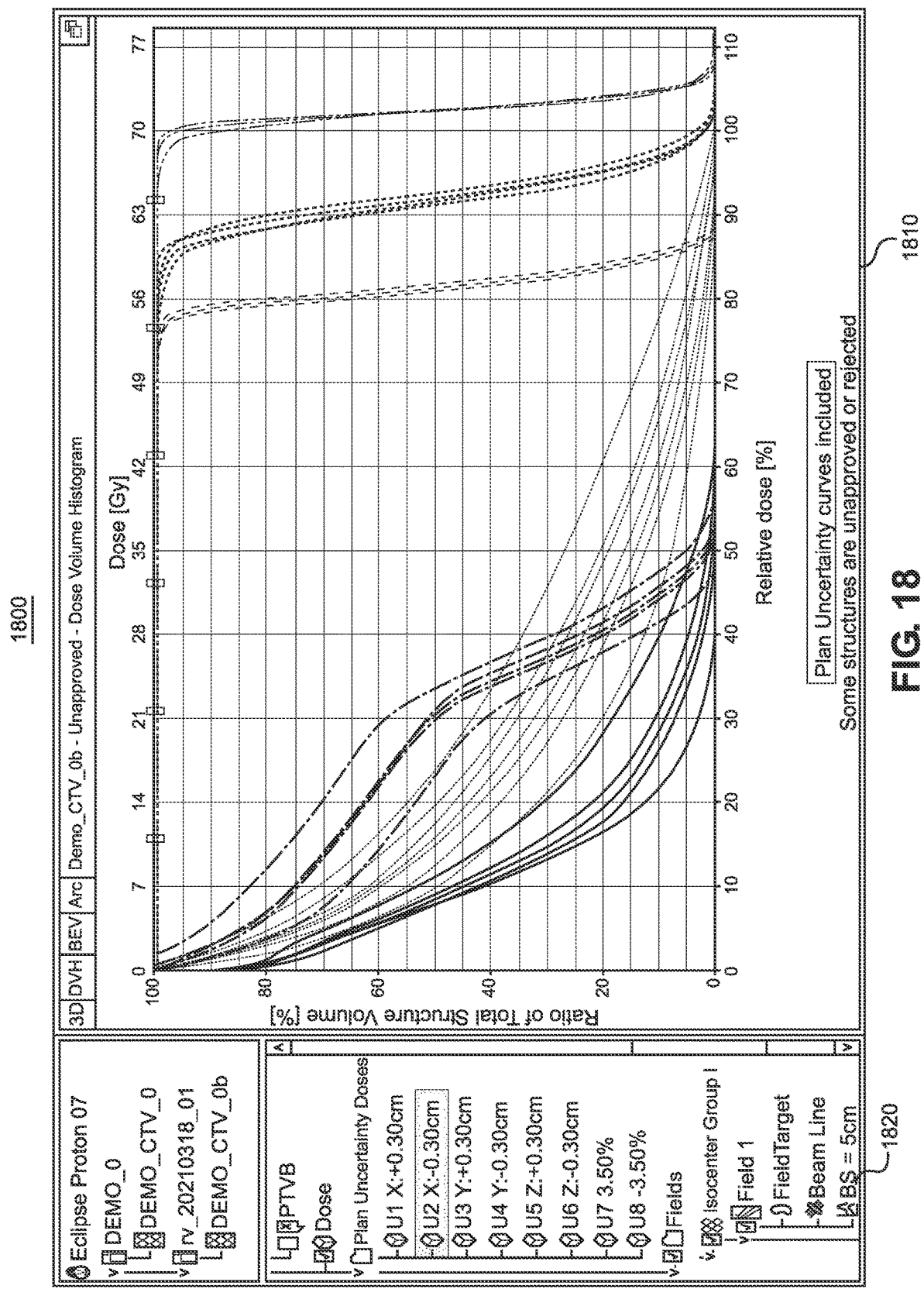
FIG. 18 is a block diagram of a GUI in accordance with one embodiment.

It is appreciated a GUI can include various additional features. FIG. 18 is a block diagram of a GUI 1800 in accordance with one embodiment. GUI 1800 includes a dose rate volume histogram 1810 and additional features 1820. The addition features 1820 can include system navigation indicators, histogram adjustment indicators, dropdown selections, and so on. In one embodiment, dose rate volume histogram 1810 is similar to dose rate volume histogram 1700.

FIG. 19 is a flow chart of treatment plan uncertainty adjustment method 1900 in accordance with one embodiment.

In block 1910, treatment plan development information is accessed. The information can be included in a knowledge base (e.g., similar to knowledge base 302, etc.). The treatment plan development information can include patient records, treatment types, and statistical models. In one exemplary implementation, accessing treatment plan development information includes accessing information related to prescription parameter values (e.g., values of a prescribed dose, dose rate, etc.) for a volume in a treatment target.

In block 1920, uncertainty information corresponding to an uncertainty associated with implementation of the treatment plan is accessed. The uncertainty information can include information associated with radiation system tolerances and setup conditions. In one embodiment, accessing uncertainty information includes presenting a GUI to a user (e.g., physician, technician, etc.), and receiving input from the user via the GUI. The GUI can be similar to the GUIs illustrated in FIGS. 15, 16, 18, and so on.

Information corresponding to uncertainties can be associated with radiation system performance tolerances and errors in setup of the treatment target. The uncertainties can be associated with at least one of radiation system performance tolerances, position of the treatment target, a beam intensity scenario, a range uncertainty, different transmission tables, and spot times.

In one exemplary implementation, respective sets of a plurality of uncertainties correspond to respective ones of a plurality of scenarios. In one exemplary implementation, information on a set of uncertainty scenarios is accessed and a dose rate distribution based upon the multiple uncertainty scenarios is determined.

In block 1930, an optimization process is performed based upon the treatment plan development information and uncertainty information. In one embodiment, an optimization process predicts a treatment plan. In one embodiment, an optimization process includes generating graphical element information, wherein the graphical element conveys a result of the optimization and potential impact of the uncertainties. The graphical element can convey an impact of the uncertainty information on a prescription parameter (e.g., dose, dose rate, etc.). A histogram based upon uncertainty considerations can be generated. In one embodiment, the graphical element includes a prescription parameter volume histogram (e.g., DVH, DRHV, DTVH, etc.). In one embodiment, graphical element information (e.g., histogram, etc.) is configured for rendering/presentation on a graphical user interface (GUI). In one embodiment, a GUI facilitates treatment planning by allowing a planner to readily visualize key elements of a proposed treatment plan (e.g., the dose rate per sub-volume), to readily visualize the effects on those elements of changes to the proposed plan, and to readily visualize a comparison between different plans.

In block 1940, finalization of a treatment plan is implemented. In one embodiment, an evaluation process is performed. Finalizing the treatment plan can include evaluating the graphical element information and analyzing robustness of the treatment plan against uncertainties. The graphical element can be a histogram and evaluation directed to the histogram. Adjustments to prescription parameter, the treatment plan are determined based on the graphical element (e.g., histogram, etc.) information. In one embodiment, wherein determining an uncertainty adjusted dose rate includes adjusting the prescribed dose rate by an uncertainty factor. The evaluation can include an analysis of robustness against uncertainties.

In one embodiment, an uncertainty indication band in a histogram (e.g., a dose volume histogram, a dose rate volume histogram, etc.) can be evaluated for robustness. In one exemplary implementation, an uncertainty indication band can be compared to threshold curves. The threshold curves can correspond to acceptable/unacceptable limits on dose and dose rate, and incidental radiation of normal/healthy tissue. In one embodiment, if a threshold curve indicates unacceptable limits and the threshold curve lies within the range of an uncertainty indication band, then the robustness of the corresponding treatment plan against uncertainties can be determined to be low/intolerable. In one exemplary implementation, treatment planning parameters can be adjusted until the threshold curve is not within the range of the uncertainty indication band.

In one embodiment, aspects of accessing uncertainty information, optimization based on the uncertainties, and corresponding histogram evaluation can be automated (e.g., by artificial assistance, expert systems, etc.). In one exemplary implementation, uncertainty values associated with radiation system and machine performance are automatically provided (e.g., automatically entered in histogram calculations, presented as suggestions to a user, etc.). In one embodiment, a radiation system/machine has machine learning capabilities that track and automatically update uncertainty values as conditions/performance change.

In one exemplary implementation, the finalization includes parameter adjustments based upon histogram analysis/evaluation. The treatment plan can be similar to treatment plan 322, similar to treatment plan resulting in block 812, and so on. In one exemplary implementation, a treatment plan (e.g., 322, etc.) is not considered a final treatment plan until adjustments corresponding to uncertainty scenarios are considered and implemented.

In one embodiment, similar to the optimization section above, a user can define the uncertainty parameter and perform uncertainty histogram evaluation. The system calculates the final dose distribution (DVH) for the different scenarios, where each scenario is represented by a dotted line and the user can determine if the worst scenario is matching the dose (or dose rate) that is expected for that structure.

It is appreciated the visualization of the dose rate robustness is not limited to two-dimensional dose rate volume histograms. In one embodiment, a visualization of the dose rate robustness can also include three-dimensional plots.

Figure 20:
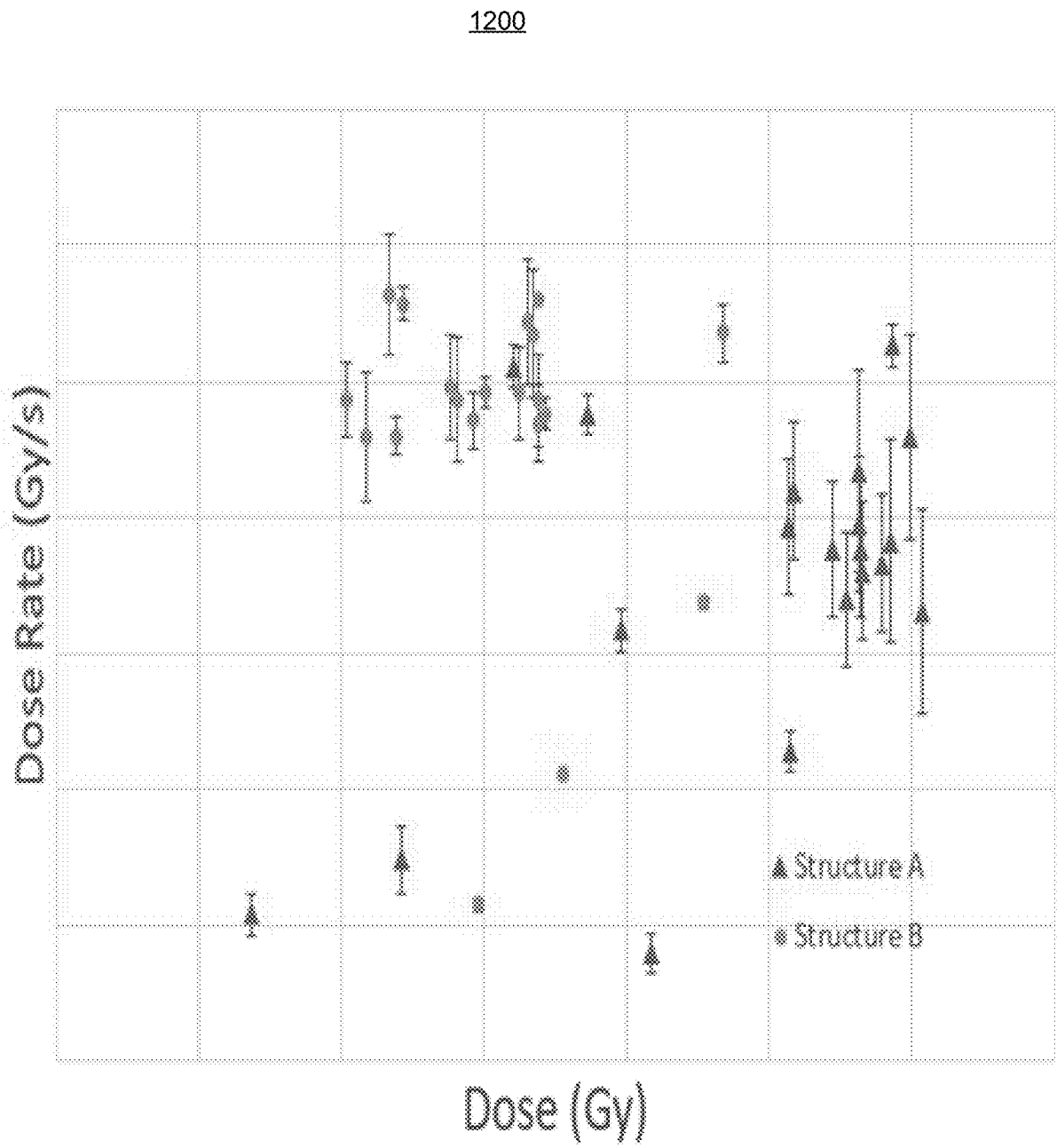
FIG. 20 is a graphical representation of dose to dose rate in accordance with one embodiment.

It is appreciated that various information can be presented in histograms. FIG. 20 is a graphical representation of a dose to dose rate correlation in accordance with one embodiment. In one embodiment, a dose and corresponding dose rate is represented by a circle for a first target (e.g., structure, tumor, etc.) and a square for a second target. The bars represent uncertainty ranges for the respective circle or square. The bars in FIG. 20 representing uncertainty ranges are displayed in a vertical orientation. It is appreciated that bars representing the uncertainty ranges can also be implemented or displayed in a horizontal orientation.

Figure 21:
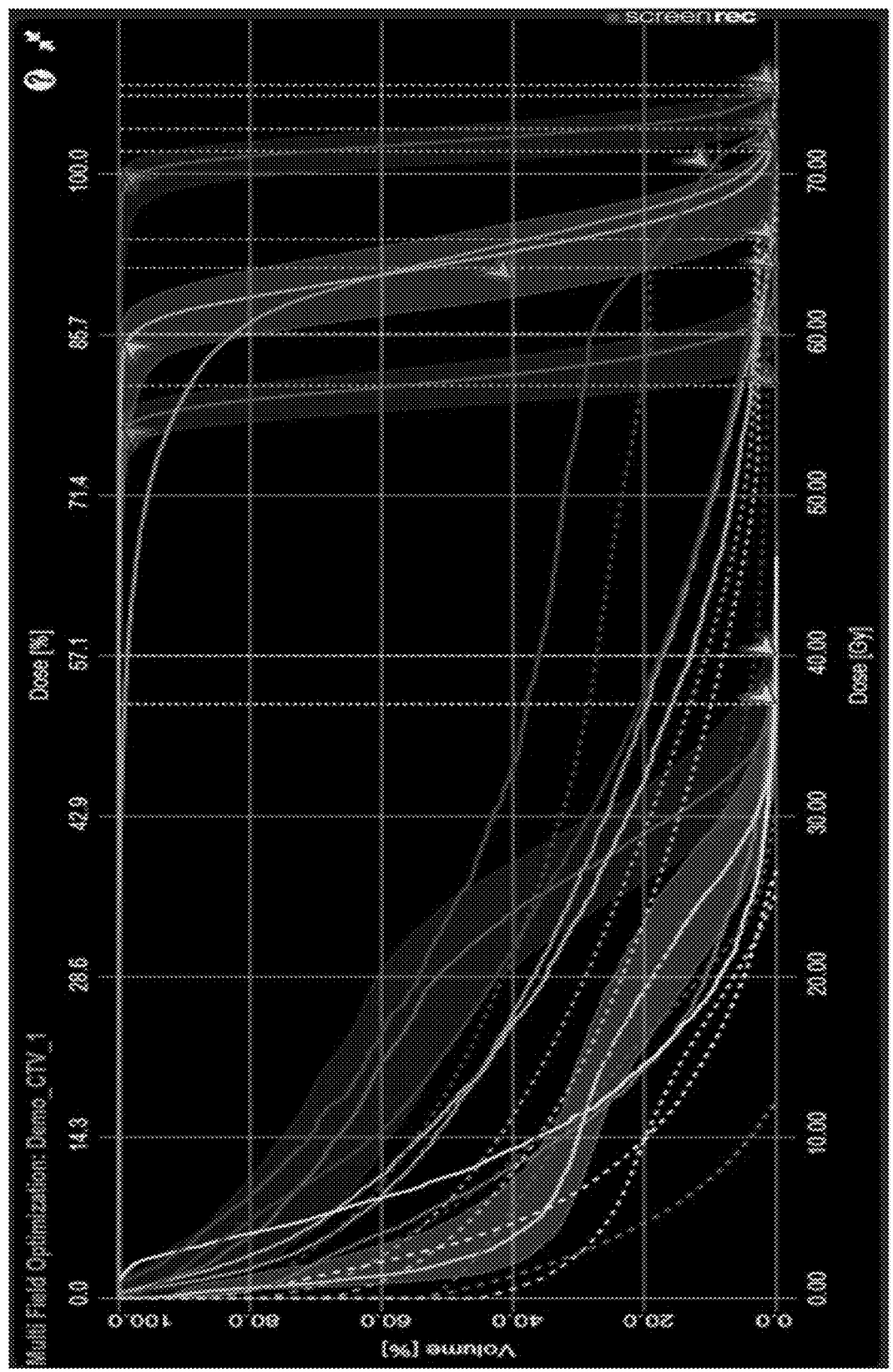
FIG. 21 is a graphical representation of another histogram in accordance with one embodiment.

FIG. 21 is a graphical representation of another histogram in accordance with one embodiment.

In addition to radiation therapy techniques in which the intensity of the particle beam is either constant or modulated across the field of delivery, such as IMRT and IMPT, embodiments according to the invention can be used in spatially fractionated radiation therapy including high-dose spatially fractionated grid radiation therapy and microbeam radiation therapy.

In one embodiment, a system and method pertain to generating and implementing a treatment plan that is the most effective (relative to other plans) and with the least (or most acceptable) side effects (e.g., a lower dose rate outside of the region being treated, etc.). Thus, an exemplary system and method can facilitate improvements in the field of radiation treatment planning specifically and the field of radiation therapy in general. In one embodiment, a system and method can allow more efficient and effective treatment plans to be generated quickly. Also, a system and method incorporating uncertainty in radiation treatment can help improve the functioning of computers because, for example, by reducing the complexity of generating treatment plans, fewer computational resources are needed and consumed, meaning also that computer resources are freed up to perform other tasks. The improvement can include expanding FLASH RT to a wider variety of treatment platforms and target sites. Treatment plans generated as described herein are superior for sparing normal tissue from radiation in comparison to conventional techniques even for non-FLASH dose rates by reducing, if not minimizing, the magnitude (and the integral in some cases) of the dose to normal tissue (outside the target) by design. When used with FLASH dose rates, management of patient motion is simplified because the doses are applied in a short period of time (e.g., less than a second). Treatment planning, while still a complex task of finding a balance between competing and related parameters, is simplified relative to conventional planning. The techniques described herein may be useful for stereotactic radiosurgery as well as stereotactic body radiotherapy with single or multiple metastases.

Although the subject matter has been described in language specific to structural features and methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
   a processor; and
   memory coupled to the processor and including instructions that, when executed, cause the processor to
   access information associated with a radiation treatment plan,
   access information corresponding to an uncertainty associated with implementation of the radiation treatment plan,
   perform an optimization process including generating a graphical element, wherein the graphical element conveys results of the optimization process including an impact of the uncertainty, wherein
   the graphical element includes a band and one or more threshold curves, and the one or more threshold curves correspond to at least one of a limit on dose, dose rate, or incidental radiation on healthy tissue, and adjust the radiation treatment plan in response to the band including the one or more threshold curves.

2. The computer system of claim 1, wherein the graphical element is a histogram.

3. The computer system of claim 1, wherein the graphical element is a dose rate volume histogram with a volume indication on a first axis and a dose rate indication on a second axis.

4. The computer system of claim 1, wherein the graphical element is a dose volume histogram with a volume indication on a first axis and a dose indication on a second axis.

5. The computer system of claim 1, wherein the uncertainty includes a tolerance variance associated with a parameter that impacts a dose rate.

6. The computer system of claim 1, wherein the uncertainty is associated with a radiation system performance tolerance.

7. The computer system of claim 1, wherein the uncertainty is associated with a patient set up.

8. The computer system of claim 1, wherein the instructions, when executed, cause the processor to finalize the radiation treatment plan, including evaluating information associated with the graphical element and analyzing robustness of the radiation treatment plan, the robustness indicating an allowance for the uncertainty of the treatment plan.

9. The computer system of claim 1, wherein the graphical element is a multifield optimization dose volume histogram that includes a plurality of uncertainty scenarios.

10. The computer system of claim 1, wherein the adjusting the radiation treatment plan increases robustness of the radiation treatment plan, the robustness indicating an allowance for the uncertainty of the treatment plan.

11. A non-transitory computer-readable storage medium having computer executable instructions for causing a computer system to perform a method, the method comprising:
ascertaining treatment plan information and corresponding uncertainty information associated with a target volume;
generating a histogram of a plurality of uncertainty adjusted optimized dose rates for the target volume in accordance with the treatment plan information and corresponding uncertainty information, wherein the histogram includes a band and one or more threshold curves and the one or more threshold curves correspond to at least one of a limit on dose, dose rate, or incidental radiation on healthy tissue;
evaluating the histogram by determining whether the band includes the one or more threshold curves; and
adjusting the treatment plan information in response to determining that the band includes the one or more threshold curves.

12. The non-transitory computer-readable storage medium of claim 11, wherein the histogram is configured to test a degree of robustness of a treatment plan, the degree of robustness indicating an allowance for the uncertainty information of the treatment plan.

13. The non-transitory computer-readable storage medium of claim 11, wherein generating the histogram includes generating a plurality of graphs, wherein respective ones of the plurality of graphs correspond to respective ones of a plurality of uncertainties that are a basis for the plurality of uncertainty adjusted optimized dose rates.

14. The non-transitory computer-readable storage medium of claim 13, wherein the plurality of graphs correspond to a dose rate band which defines a region in which a graph curve for an actual treatment lies.

15. The non-transitory computer-readable storage medium of claim 11, wherein a proportion of irradiated volume receiving a threshold dose rate Dth and the dose rate received by (100–p) percent of the irradiated volume is displayed for uncertainty scenarios associated with the histogram.

16. The non-transitory computer-readable storage medium of claim 11, wherein the uncertainty information is associated with at least one of radiation system performance tolerances, position of a treatment target, a beam intensity scenario, a range uncertainty, different transmission tables, or spot times.

17. The non-transitory computer-readable storage medium of claim 11, wherein the histogram is included in a graphical user interface (GUI).

18. The non-transitory computer-readable storage medium of claim 11, wherein the evaluating the histogram includes analyzing whether a dose rate prescription is met for the target volume and healthy tissue.

19. A radiation system comprising:
an accelerator configured to generate radiation and direct the radiation towards a treatment target;
a control component configured to control the accelerator in accordance with a radiation treatment plan;
a computer system including
a processor, and
memory coupled to the processor and including instructions that, when executed, cause the processor to generate the radiation treatment plan by
ascertaining treatment plan and uncertainty scenario information,
determining a dose rate distribution based upon the uncertainty scenario information,
generating a histogram visualization of the dose rate distribution based upon the uncertainty scenario information, the histogram visualization including a band and one or more threshold curves, the one or more threshold curves corresponding to at least one of a limit on dose, dose rate, or incidental radiation on healthy tissue, and
adjusting the radiation treatment plan in response to the band including the one or more threshold curves.

20. The radiation system of claim 19, wherein generating the radiation treatment plan further comprises displaying a dose rate volume histogram and parameters for regions of interest.

21. The radiation system of claim 19, wherein generating the radiation treatment plan further includes checking whether a dose rate prescription is met for the treatment target and healthy tissue.

* * * * *